(12) United States Patent
Solem et al.

(10) Patent No.: US 7,500,989 B2
(45) Date of Patent: Mar. 10, 2009

(54) DEVICES AND METHODS FOR PERCUTANEOUS REPAIR OF THE MITRAL VALVE VIA THE CORONARY SINUS

(75) Inventors: Jan Otto Solem, Stetten (CH); Per Ola Kimblad, Lund (SE); Sepehr Fariabi, Newport Coast, CA (US); Stefan Schreck, Vista, CA (US); Vaso Adzich, Santa Ana, CA (US); Octavian Iancea, Irvine, CA (US)

(73) Assignee: Edwards Lifesciences Corp., Irvine, CA (US)

( * ) Notice: Subject to any disclaimer, the term of this patent is extended or adjusted under 35 U.S.C. 154(b) by 262 days.

(21) Appl. No.: 11/144,521

(22) Filed: Jun. 3, 2005
(Under 37 CFR 1.47)

(65) Prior Publication Data

US 2006/0276890 A1    Dec. 7, 2006

(51) Int. Cl.
*A61F 2/24* (2006.01)
(52) U.S. Cl. ..................... 623/2.37; 623/2.36
(58) Field of Classification Search ............... 606/144, 606/151, 157, 158; 623/1.11, 1.23
See application file for complete search history.

(56) References Cited

U.S. PATENT DOCUMENTS

| | | | |
|---|---|---|---|
| 4,655,771 A | 4/1987 | Wallsten | |
| 5,064,435 A | 11/1991 | Porter | |
| 5,071,407 A | 12/1991 | Termin et al. | |
| 5,170,802 A | 12/1992 | Mehra | |
| 5,209,730 A | 5/1993 | Sullivan | |
| 5,224,491 A | 7/1993 | Mehra | |
| 5,304,131 A | 4/1994 | Paskar | |
| 5,382,259 A | 1/1995 | Phelps et al. | |
| 5,383,892 A | 1/1995 | Cardon et al. | |
| 5,390,661 A | 2/1995 | Griffith et al. | |
| 5,441,515 A | 8/1995 | Khosravi et al. | |

(Continued)

FOREIGN PATENT DOCUMENTS

WO     WO 96/34211     10/1996

(Continued)

OTHER PUBLICATIONS

Buchanan, et al., Circumferential Suture of the Mitral Annulus for Correction of Mitral Regurgitation in Dogs, Veterinary Surgery, 27:182-193, 1998.

*Primary Examiner*—William H. Matthews
*Assistant Examiner*—Suba Ganesan
(74) *Attorney, Agent, or Firm*—David L. Hauser

(57) ABSTRACT

Devices and methods for treating mitral regurgitation by reshaping the mitral annulus in a heart. One preferred device for reshaping the mitral annulus is provided as an elongate body having dimensions as to be insertable into a coronary sinus. The elongate body includes a proximal frame having a proximal anchor and a distal frame having a distal anchor. A ratcheting strip is attached to the distal frame and an accepting member is attached to the proximal frame, wherein the accepting member is adapted for engagement with the ratcheting strip. An actuating member is provided for pulling the ratcheting strip relative to the proximal anchor after deployment in the coronary sinus. In one preferred embodiment, the ratcheting strip is pulled through the proximal anchor for pulling the proximal and distal anchors together, thereby reshaping the mitral annulus.

14 Claims, 22 Drawing Sheets

U.S. PATENT DOCUMENTS

| | | |
|---|---|---|
| 5,449,373 A | 9/1995 | Pinchasik et al. |
| 5,496,275 A | 3/1996 | Sirhan et al. |
| 5,531,779 A | 7/1996 | Dahl et al. |
| 5,545,209 A | 8/1996 | Roberts et al. |
| 5,591,197 A | 1/1997 | Orth et al. |
| 5,607,444 A | 3/1997 | Lam |
| 5,713,949 A | 2/1998 | Jayaraman |
| 5,817,126 A | 10/1998 | Imran |
| 5,876,433 A | 3/1999 | Lunn |
| 5,891,108 A | 4/1999 | Leone et al. |
| 5,935,081 A | 8/1999 | Kadhiresan |
| 5,954,761 A | 9/1999 | Machek et al. |
| 5,961,545 A | 10/1999 | Lentz et al. |
| 5,980,522 A | 11/1999 | Koros et al. |
| 6,006,122 A | 12/1999 | Smits |
| 6,013,854 A | 1/2000 | Moriuchi |
| 6,019,739 A | 2/2000 | Rhee et al. |
| 6,051,020 A | 4/2000 | Goicoechea et al. |
| 6,077,296 A | 6/2000 | Shokoohi et al. |
| 6,093,203 A | 7/2000 | Uflacker |
| 6,110,100 A | 8/2000 | Talpade |
| 6,123,699 A | 9/2000 | Webster, Jr. |
| 6,161,029 A | 12/2000 | Spreigl et al. |
| 6,161,543 A | 12/2000 | Cox et al. |
| 6,165,169 A | 12/2000 | Panescu et al. |
| 6,168,619 B1 | 1/2001 | Dinh et al. |
| 6,171,329 B1 | 1/2001 | Shaw et al. |
| 6,210,432 B1 | 4/2001 | Solem et al. |
| 6,368,348 B1 | 4/2002 | Gabbay |
| 6,402,781 B1 | 6/2002 | Langberg et al. |
| 6,537,314 B2 | 3/2003 | Langberg et al. |
| 6,569,198 B1 | 5/2003 | Wilson et al. |
| 6,629,534 B1 | 10/2003 | St. Goar et al. |
| 6,656,221 B2 | 12/2003 | Taylor et al. |
| 6,676,702 B2 | 1/2004 | Mathis |
| 6,706,065 B2 | 3/2004 | Langberg et al. |
| 6,709,456 B2 | 3/2004 | Langberg et al. |
| 6,764,510 B2 | 7/2004 | Vidlund et al. |
| 6,790,231 B2 | 9/2004 | Liddicoat et al. |
| 6,800,090 B2 | 10/2004 | Alferness et al. |
| 6,810,882 B2 | 11/2004 | Langberg et al. |
| 6,890,353 B2 | 5/2005 | Cohn et al. |
| 6,908,478 B2 | 6/2005 | Alferness et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,044,967 B1 | 5/2006 | Solem et al. |
| 7,090,695 B2 | 8/2006 | Solem et al. |
| 2001/0018611 A1 | 8/2001 | Solem et al. |
| 2002/0019660 A1 | 2/2002 | Gianotti et al. |
| 2002/0087173 A1 | 7/2002 | Alferness et al. |
| 2002/0111647 A1 | 8/2002 | Khairkhahan et al. |
| 2002/0183838 A1 | 12/2002 | Liddicoat et al. |
| 2002/0188170 A1 | 12/2002 | Santamore et al. |
| 2003/0083538 A1* | 5/2003 | Adams et al. .................. 600/16 |
| 2003/0120341 A1 | 6/2003 | Shennib et al. |
| 2003/0135267 A1 | 7/2003 | Solem et al. |
| 2003/0171806 A1 | 9/2003 | Mathis et al. |
| 2003/0204138 A1 | 10/2003 | Choi |
| 2004/0073302 A1 | 4/2004 | Rourke et al. |
| 2004/0102840 A1 | 5/2004 | Solem et al. |
| 2004/0102841 A1 | 5/2004 | Langberg et al. |
| 2004/0133220 A1 | 7/2004 | Lashinski et al. |
| 2004/0138744 A1 | 7/2004 | Lashinski et al. |
| 2004/0167546 A1* | 8/2004 | Saadat et al. ................ 606/144 |
| 2004/0176840 A1 | 9/2004 | Langberg et al. |
| 2004/0186566 A1* | 9/2004 | Hindrichs et al. .......... 623/2.37 |
| 2004/0254600 A1 | 12/2004 | Zarbatany et al. |
| 2005/0043792 A1 | 2/2005 | Solem et al. |
| 2005/0060030 A1 | 3/2005 | Lashinski et al. |
| 2005/0080483 A1 | 4/2005 | Solem et al. |
| 2005/0096740 A1 | 5/2005 | Langberg et al. |
| 2005/0177228 A1 | 8/2005 | Solem et al. |
| 2005/0222678 A1 | 10/2005 | Lashinski et al. |
| 2006/0116756 A1 | 6/2006 | Solem et al. |
| 2006/0116757 A1 | 6/2006 | Lashinski et al. |
| 2006/0129051 A1 | 6/2006 | Rowe et al. |
| 2006/0184230 A1 | 8/2006 | Solem et al. |

FOREIGN PATENT DOCUMENTS

| | | |
|---|---|---|
| WO | WO 98/51365 | 11/1998 |
| WO | WO 99/44534 | 9/1999 |
| WO | WO 00/18320 | 4/2000 |
| WO | WO 01/00111 A1 | 1/2001 |
| WO | WO 01/89426 A1 | 11/2001 |
| WO | WO 02/060352 A1 | 8/2002 |
| WO | WO 02/076284 A2 | 10/2002 |
| WO | WO 02/078576 A2 | 10/2002 |
| WO | WO 03/037171 A2 | 5/2003 |
| WO | WO 2004/019816 A2 | 3/2004 |
| WO | WO 2004/045463 A2 | 6/2004 |

* cited by examiner

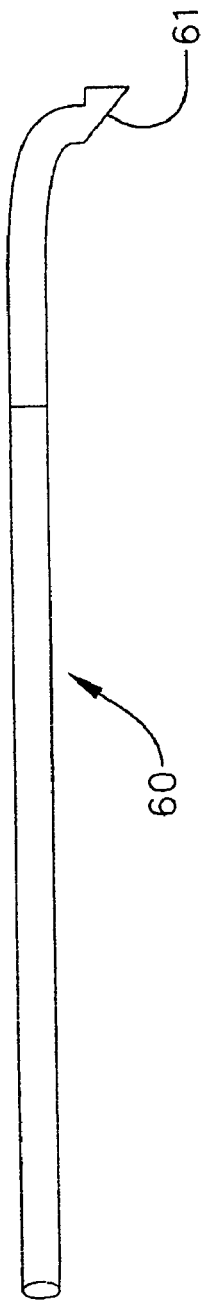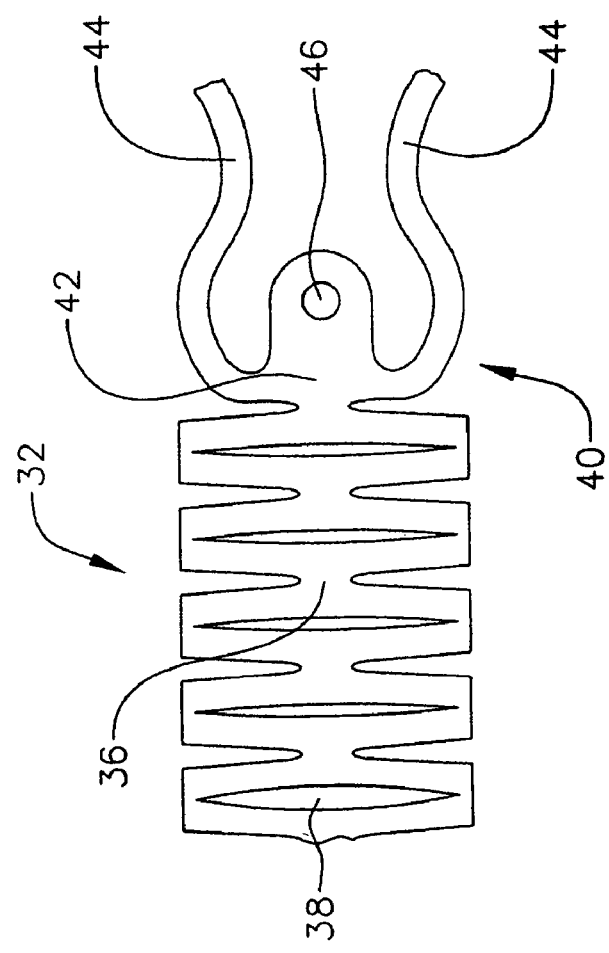
FIG.2B
FIG.2C

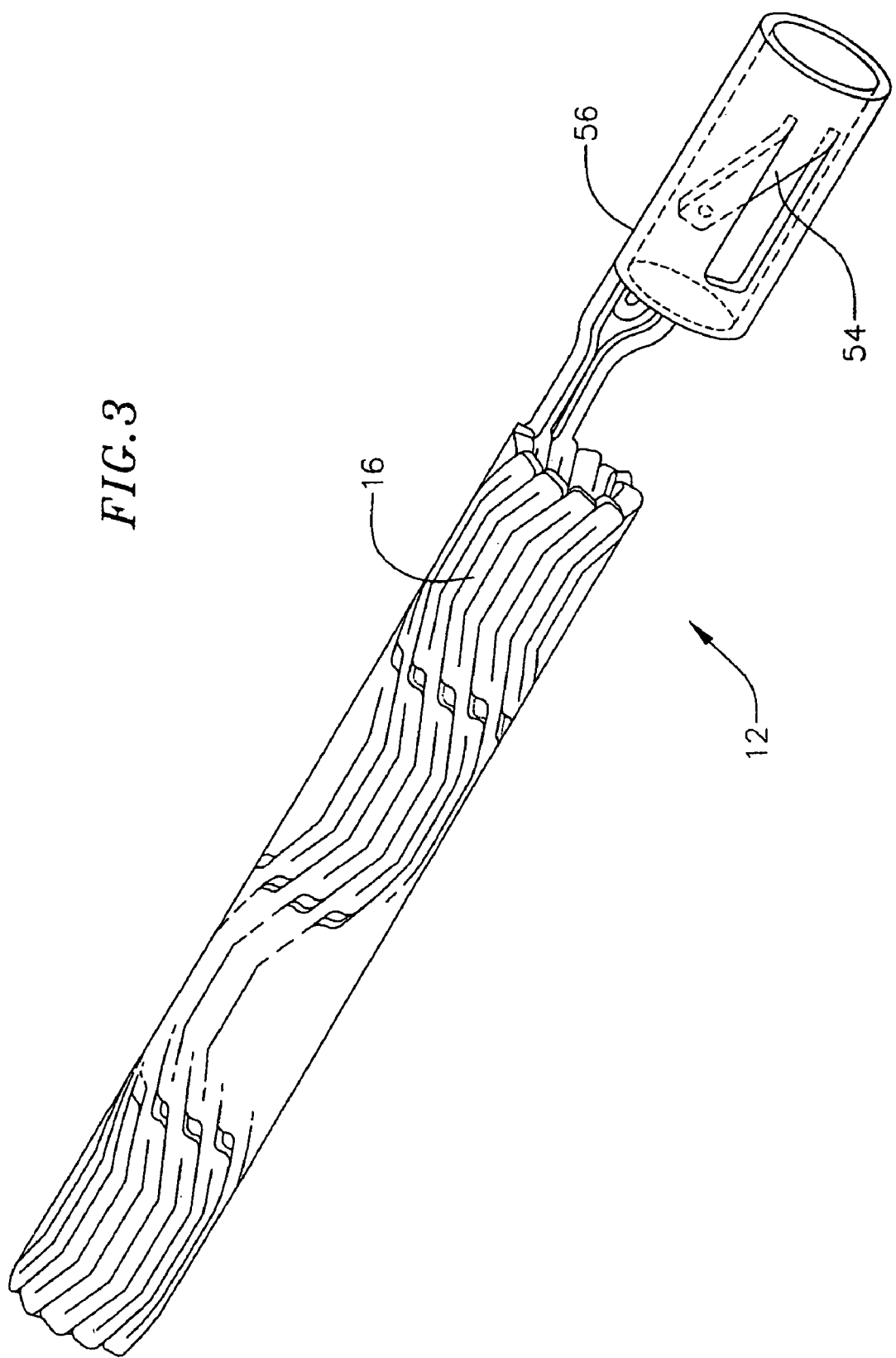

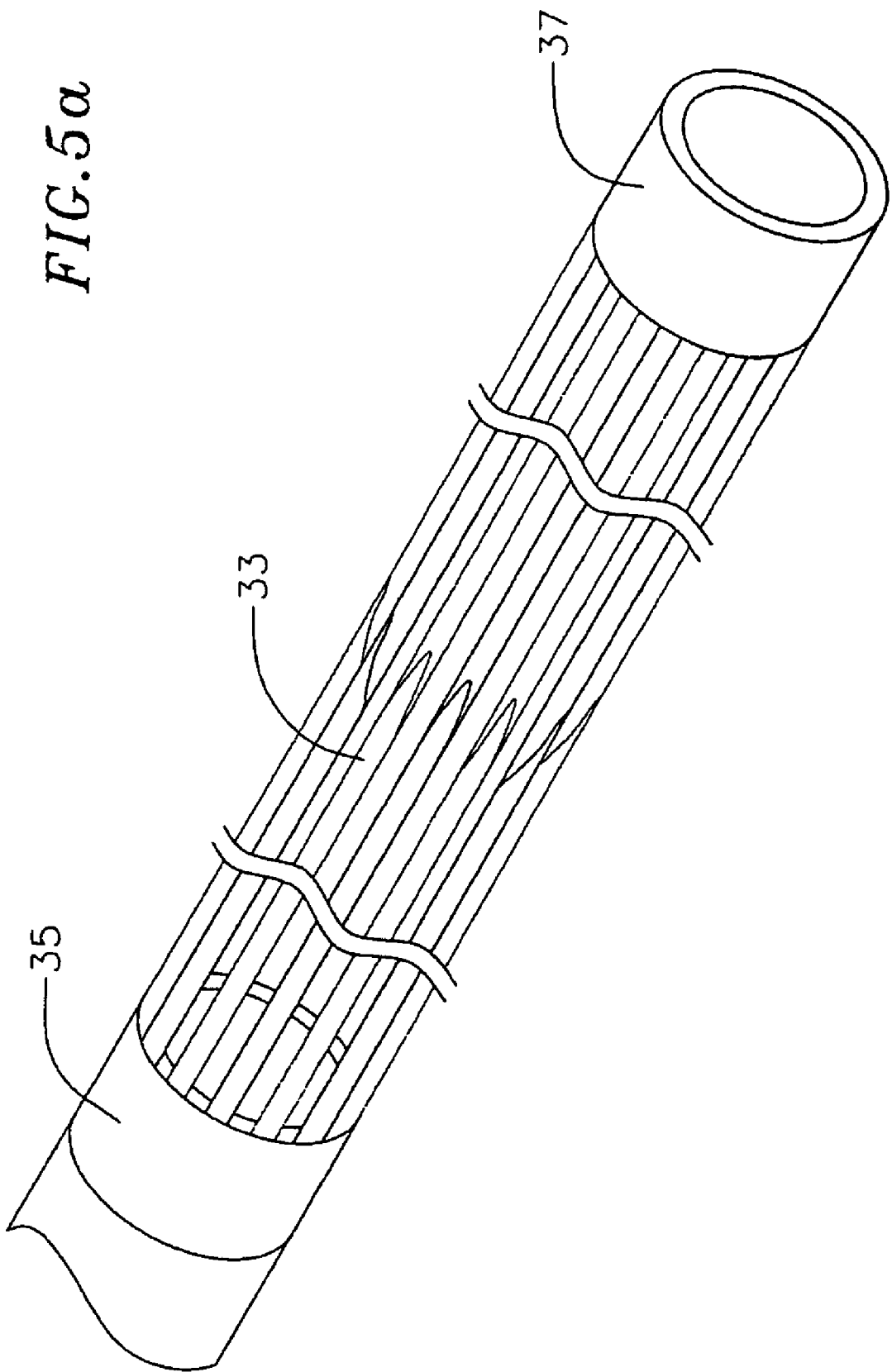

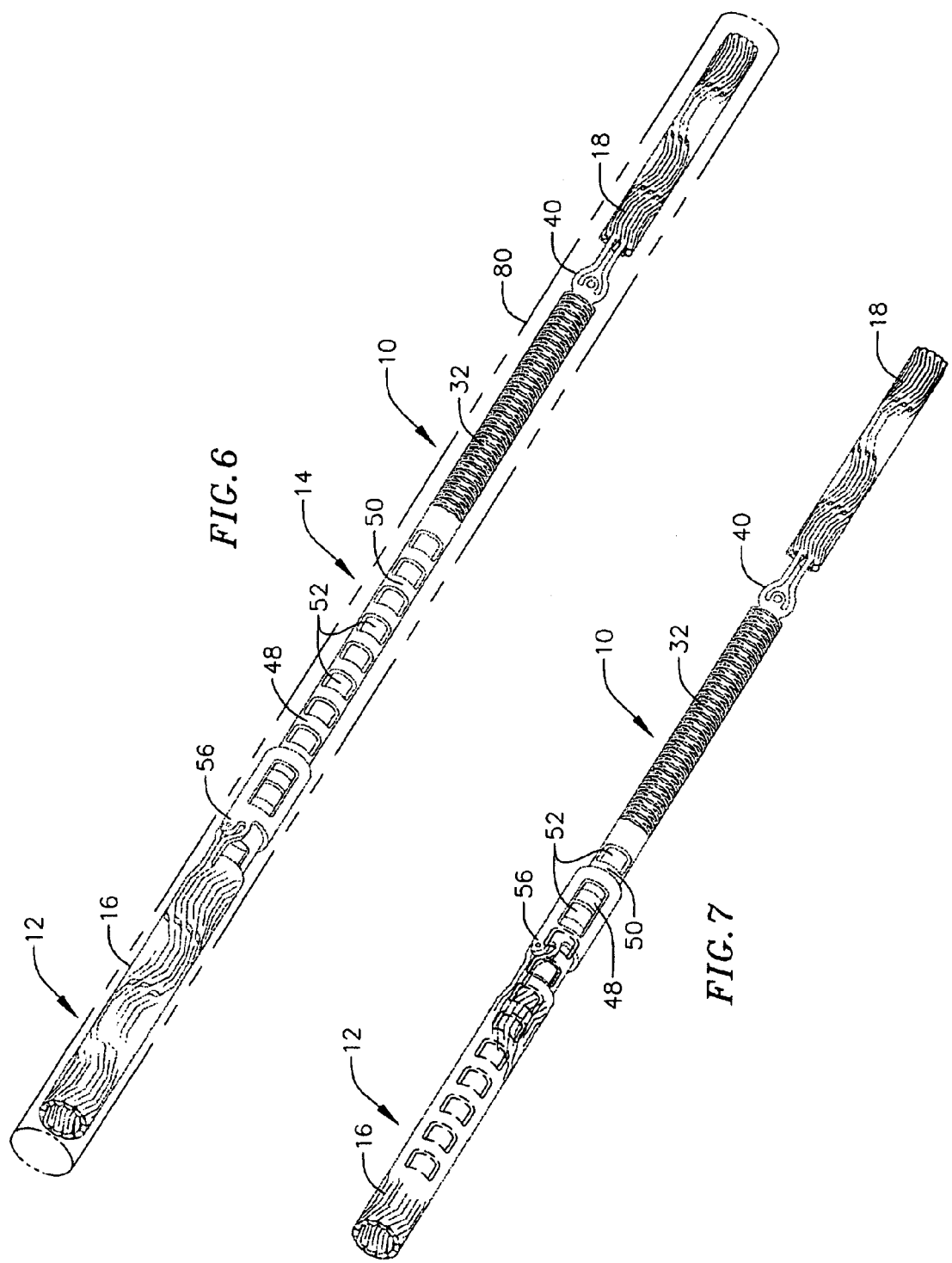

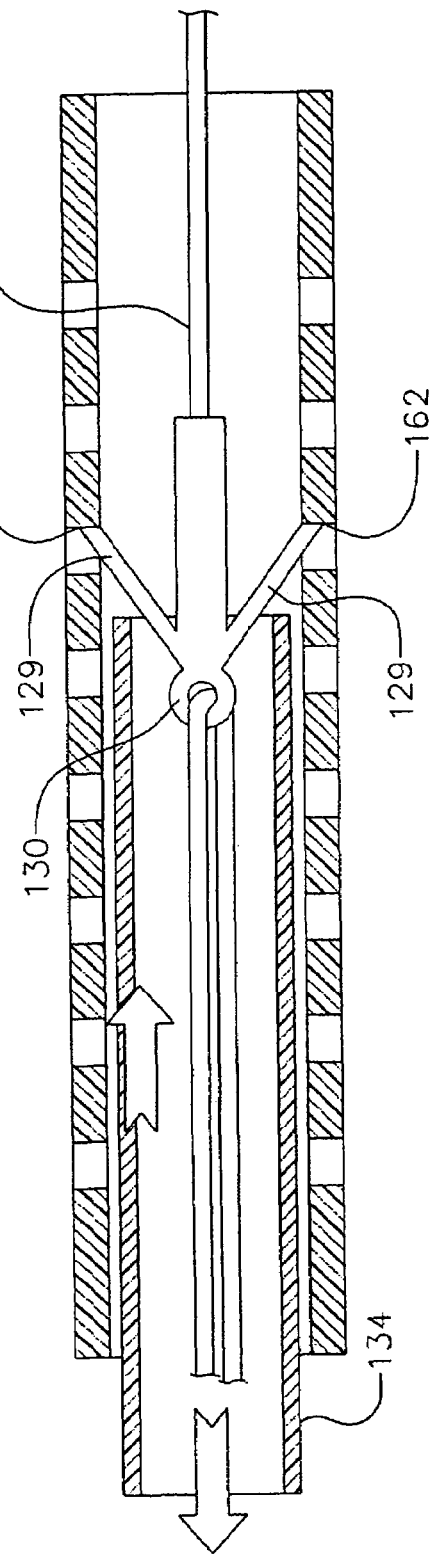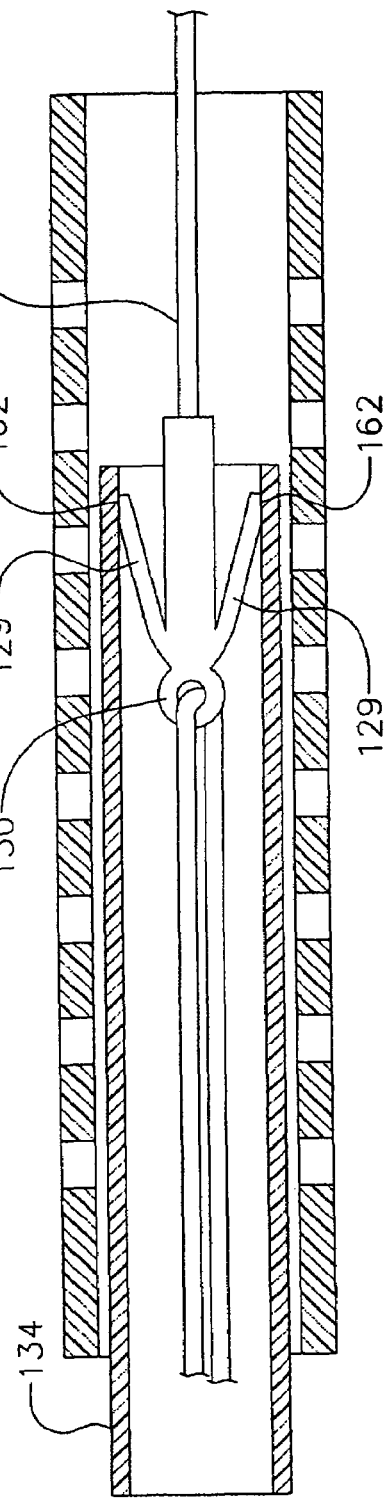

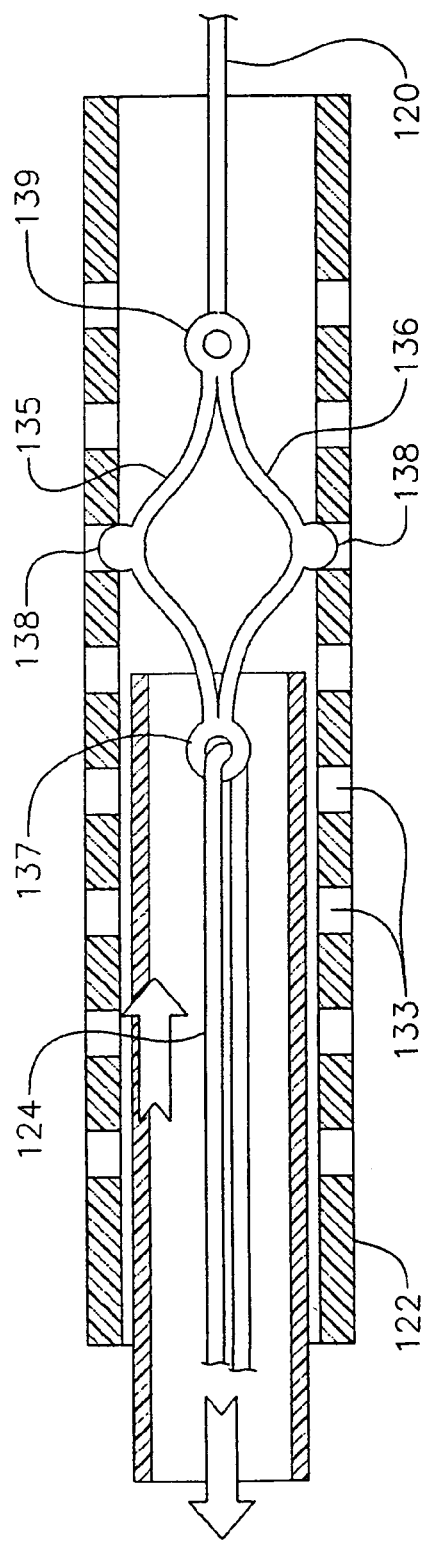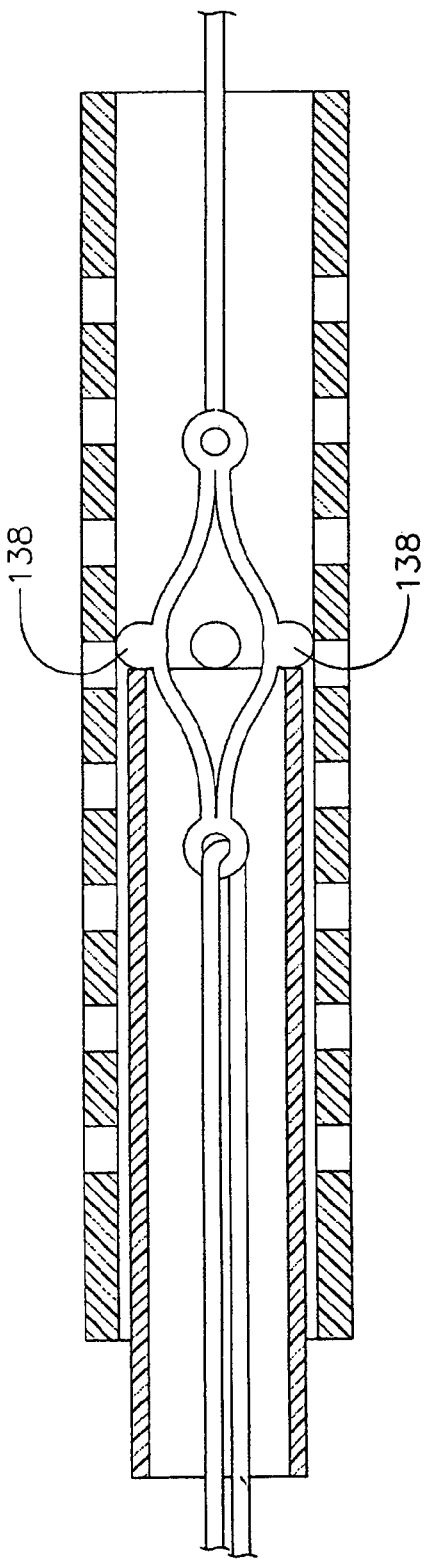

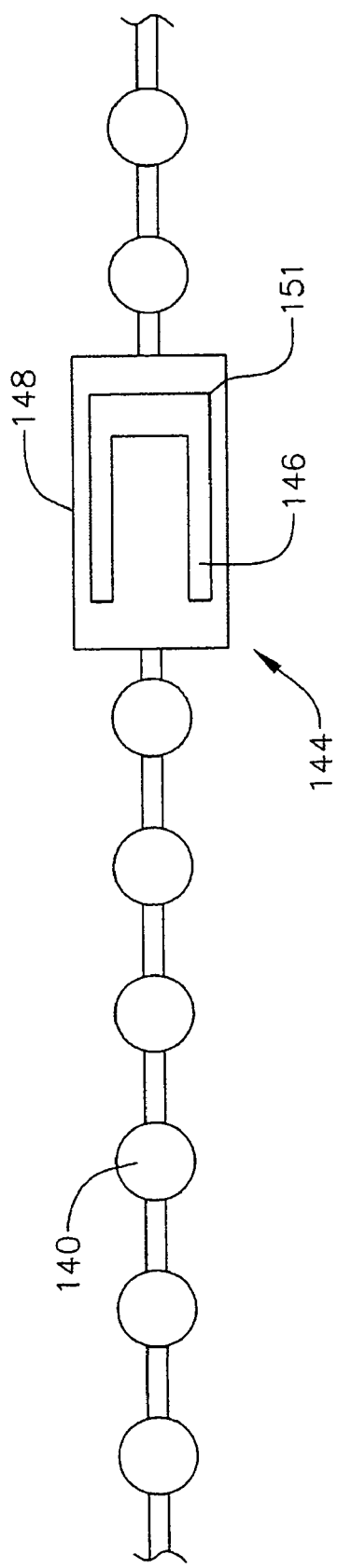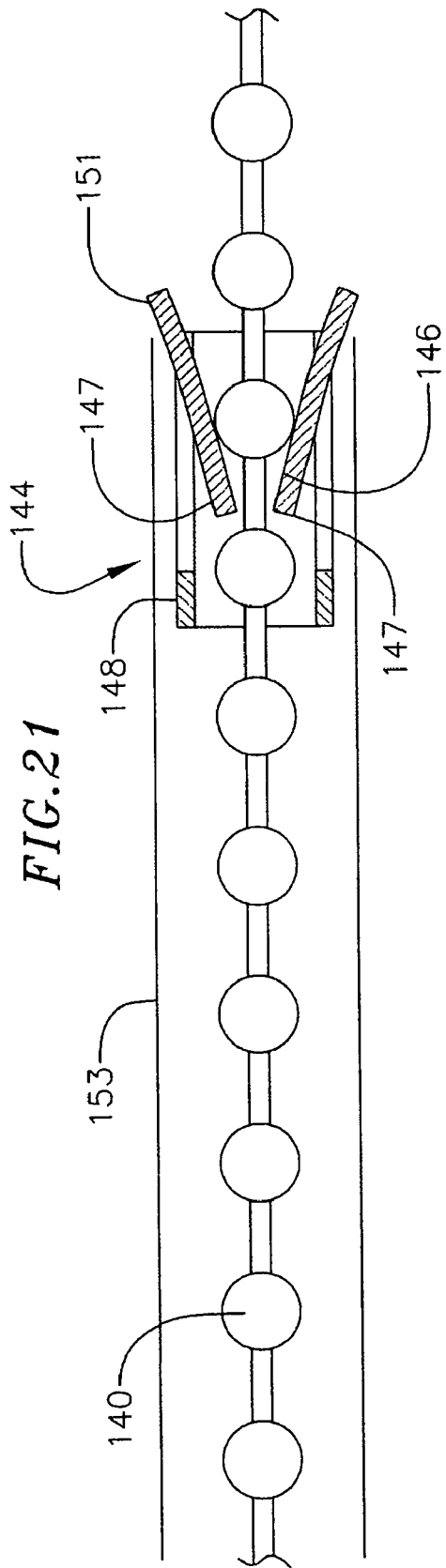

DEVICES AND METHODS FOR PERCUTANEOUS REPAIR OF THE MITRAL VALVE VIA THE CORONARY SINUS

BACKGROUND OF THE INVENTION

1. Field of the Invention

This invention generally relates to devices and methods for heart valve repair and, more particularly, to endovascular devices and methods for interventional repair of the mitral valve via the coronary sinus.

2. Description of the Related Art

Heart valve regurgitation occurs when a heart valve does not close tightly, thereby allowing blood to flow backward in the heart. Heart valve regurgitation typically occurs in the mitral valve, located between the left atrium and left ventricle, or in the tricuspid valve, located between the right atrium and right ventricle. Regurgitation in the mitral valve may result from changes in the geometric configurations of the left ventricle, papillary muscles and/or mitral annulus. Similarly, regurgitation in the tricuspid valve is caused by changes in the geometric configurations of the right ventricle, papillary muscles and/or tricuspid annulus. These geometric alterations result in mitral and tricuspid leaflet tethering and incomplete coaptation during systole.

Heart valve repair is the procedure of choice to correct heart valve regurgitation of all etiologies. With the use of current surgical techniques, it has been found that between 40% and 60% of regurgitant heart valves can be repaired, depending on the surgeon's experience and the anatomic conditions present. Heart valve repair is generally preferred over heart valve replacement due to better preservation of cardiac function and reduced risk of anticoagulant-related hemorrhage, thromboembolism and endocarditis.

In recent years, several new minimally invasive techniques have been developed for repairing heart valves without the need for surgery. Some of these techniques involve introducing systems for remodeling the mitral annulus through a blood vessel known as the coronary sinus. The coronary sinus commences at the coronary ostium in the right atrium and passes through the atrioventricular groove in close proximity to the posterior, lateral and medial aspects of the mitral annulus. Because of its position adjacent to the mitral annulus, the coronary sinus provides an ideal conduit for positioning and deploying an endovascular prosthesis to reshape the mitral annulus.

One example of a minimally invasive technique for mitral valve repair can be found in U.S. Pat. No. 6,402,781 issued to Langberg et al. ("the '781 patent"). The '781 patent describes a prosthesis deployed into the coronary sinus via a delivery catheter. The prosthesis includes an elongate body, a forming element and a lock. After the prosthesis is deployed in the coronary sinus, the forming element is withdrawn proximally to adjust the shape of the elongate body and thereby reshape the coronary sinus and mitral annulus. After sufficient adjustment, the forming element may be locked to hold the elongate body in a desired shape.

Despite the recent developments in the field of minimally invasive mitral valve repair, an urgent need still exists for an improved device that can be more easily and more reliably manipulated within the coronary sinus for reshaping the mitral annulus. It is also desirable that such a device allow the mitral valve to be reshaped in a precise and controlled manner for improving valve function and minimizing or eliminating regurgitation. Additionally, there is a need for a device that can be adjusted within the coronary sinus after a period of time has passed from the initial insertion, either to increase or decrease the amount of tension they apply to the coronary sinus. Still further, there is a need for a device that is less traumatic to the coronary sinus, both during and after their insertion into the coronary sinus, and also for a device that is reliable over long periods of time. The present invention addresses these needs.

SUMMARY OF THE INVENTION

One embodiment of the present invention is a device for the treatment of mitral annulus dilatation comprising an elongate body having dimensions as to be insertable into a coronary sinus. The elongate body includes a proximal frame having a proximal anchor and a distal frame having a distal anchor, the proximal and distal anchors being transferable between a first compressed state and a second expanded state. The elongate body further includes a ratcheting strip attached to the distal frame, the ratcheting strip having alternating engagement portions and openings, an accepting member attached to the proximal frame, the accepting member insertable into the openings of the ratcheting strip and adapted to engage the engagement portions, and an actuating member being adapted to engage the ratcheting strip and to move the ratcheting strip relative to the proximal anchor. The diameters of the proximal anchor and the distal anchor are greater in the second state than in the first state and the proximal anchor is adapted to allow the ratcheting strip to be pulled through it.

In an alternate embodiment, the device comprises, in addition to proximal and distal anchors as described above, a locking shaft attached to the proximal anchor, the locking shaft having alternating engagement portions and openings, a cinching thread attached to the distal anchor, a locking pin attached to the cinching thread, the locking pin having a plurality of locking segments insertable into the openings of the locking shaft and adapted to engage the engagement portions, and a pull line attached to the locking pin, the pull line adapted to move the locking pin relative to the locking shaft.

In another alternate embodiment, the device comprises, in addition to proximal and distal anchors as described above, a housing attached to the proximal anchor, the housing having jaws transferable between a closed state and an open state, and a cinching suture attached to the distal anchor, the cinching suture having beads spaced thereon. In this embodiment, the jaws are biased to be in the closed state.

In yet another alternate embodiment, the device includes a locking mechanism having transverse beam structures. A cinching thread having a series of conical elements is woven through the locking mechanism, allowing for the distance between a proximal and distal anchor to be shortened.

A method for reducing mitral valve regurgitation includes inserting an elongate body as described above into the coronary sinus, expanding the proximal and distal anchors of the elongate body, and moving the distal anchor relative to the proximal anchor using an actuating mechanism or pull line.

BRIEF DESCRIPTION OF THE DRAWINGS

FIG. 2b is a side view of an embodiment of an actuating member of the present invention.

FIG. 2c is an enlarged flattened view of a link and a portion of a bridge of the distal frame of FIG. 2a.

FIG. 3 is a side view of an embodiment of a proximal frame of the present invention.

FIG. 5a is a perspective view of an alternate anchor in a compressed state according to the present invention.

FIG. 6 is a side view of an elongate body of the present invention in an extended state including the distal frame and the proximal frame, the elongate body being enclosed in a delivery sheath.

FIG. 7 is a side view of an elongate body of the present invention in a contracted state including the distal frame and proximal frame.

FIG. 14a is a side view of an alternate embodiment of the proximal end of the elongate body of FIG. 11 including a pull loop.

FIG. 14b is a side view of an actuating member used to snare the pull loop shown in FIG. 14a.

FIG. 16 is a side view of the locking mechanism of FIG. 12 in the open position.

FIG. 17 is a side view of the locking mechanism of FIG. 12 in the closed position.

FIG. 18 is a side view of an alternate embodiment of a locking mechanism of the present invention in the open position.

FIG. 19 is a side view of the embodiment of FIG. 18 with the locking mechanism in the closed position.

FIG. 20 is a top view of an alternate embodiment of a locking mechanism of the present invention in the open position.

FIG. 21 is a side view of the locking mechanism of FIG. 20 in the closed position.

DETAILED DESCRIPTION OF THE PREFERRED EMBODIMENTS

Figure 1:
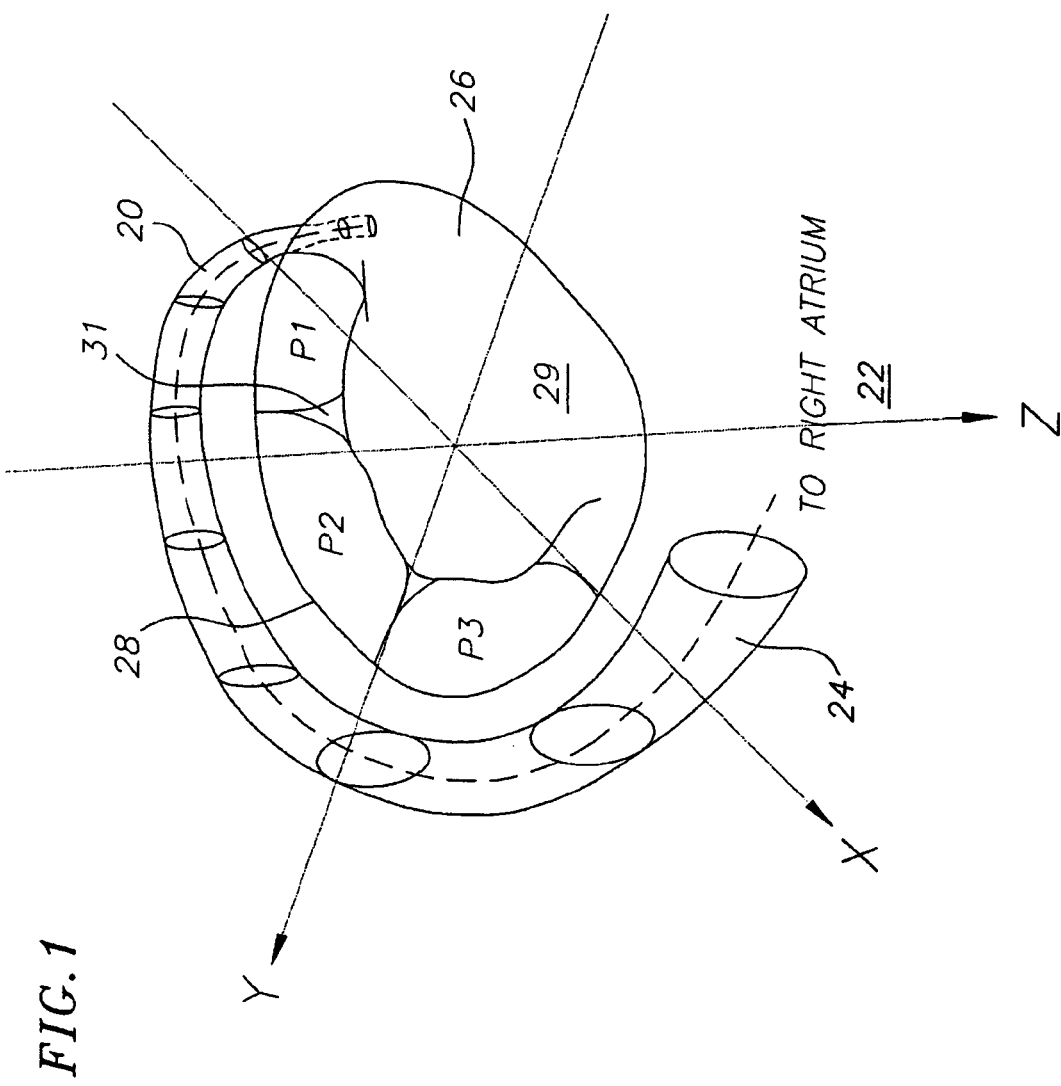
FIG. 1 is a three-dimensional view of the mitral valve and coronary sinus.

With reference now to FIG. 1, a coronary sinus 20 extends from a right atrium 22 and a coronary ostium 24 and wraps around a mitral valve 26. The term coronary sinus 20 is used herein as a generic term to describe a portion of the vena return system that is situated adjacent to the mitral valve 26 along the atrioventricular groove. The term coronary sinus 20 used herein generally includes the coronary sinus, the great cardiac vein and the anterior intraventricular vein. A mitral annulus 28 is a portion of tissue surrounding a mitral valve orifice to which several leaflets attach. The mitral valve 26 has two leaflets, namely an anterior leaflet 29 and a posterior leaflet 31. The posterior leaflet includes three scallops P1, P2 and P3.

The problem of mitral regurgitation typically results when a posterior aspect of the mitral annulus 28 dilates (i.e., enlarges), thereby displacing one or more of the posterior leaflet scallops P1, P2 or P3 away from the anterior leaflet 29. The displacement of the scallops away from the anterior leaflet causes a gap to be formed such that the mitral valve fails to close completely. The incomplete closure of the mitral valve results in mitral regurgitation. To reduce or eliminate mitral regurgitation, it is desirable to move the posterior aspect of the mitral annulus 28 in an anterior direction and close the gap caused by the leaflet displacement. As used herein, "distal" means the direction of the device as it is being inserted into a patient's body or a point of reference closer to the leading end of the device as it is inserted into a patient's body. Similarly, as used herein "proximal" means the direction of the device as it is being removed from a patient's body or a point of reference closer to a trailing end of a device as it is inserted into a patient's body.

Figure 2:
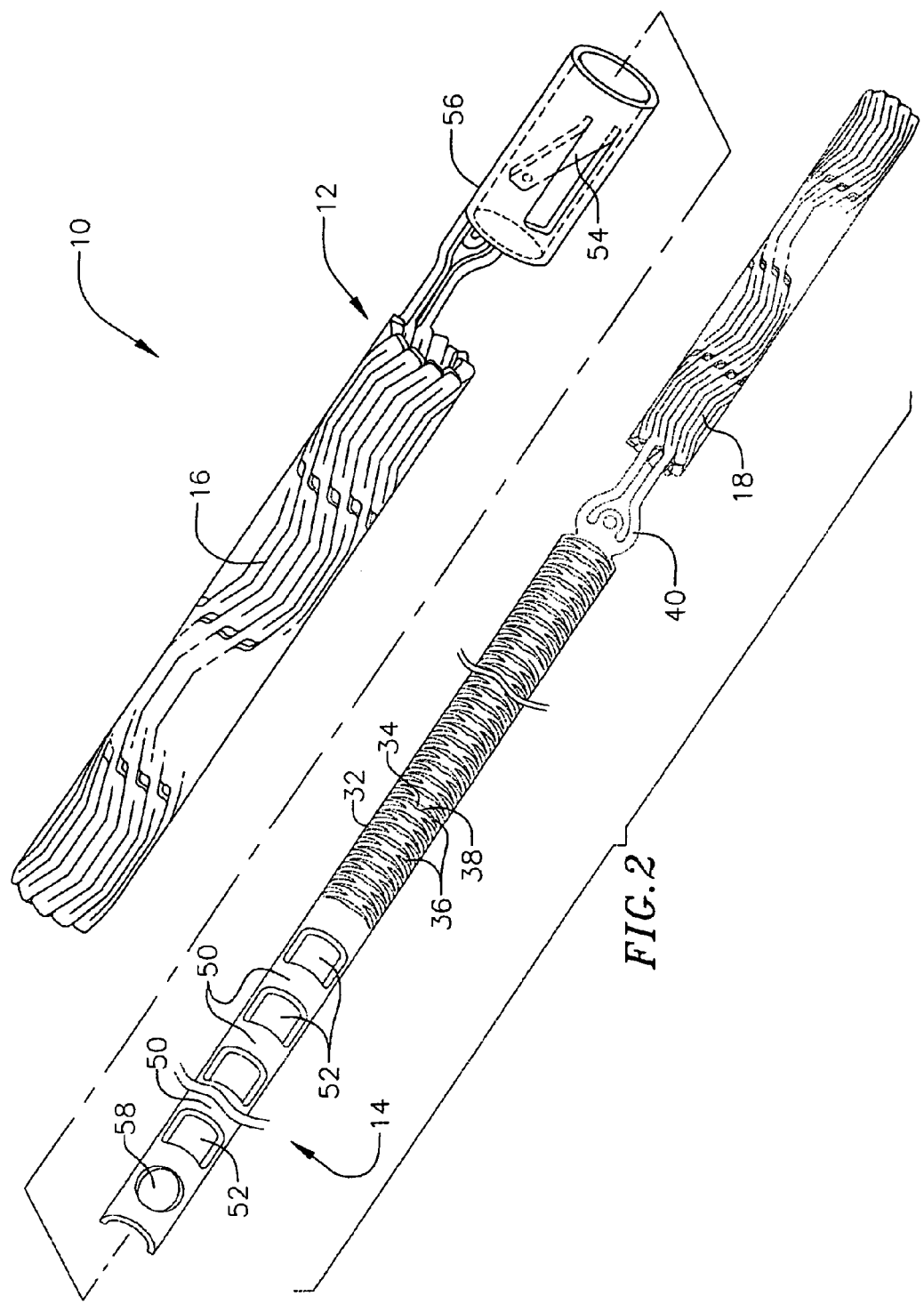
FIG. 2 is an exploded view of an embodiment of a mitral valve repair device of the present invention.

With reference now to FIG. 2, one preferred embodiment of the present invention is provided as an elongate body 10 shaped for percutaneous insertion into a coronary sinus. The elongate body includes a distal frame 14 having a distal anchor 18 and a proximal frame 12 having a proximal anchor 16. As will be explained in more detail below, a proximal end of the distal frame 14 is configured to be slidably received within a distal end of the proximal frame 12 such that the elongate body is longitudinally adjustable. Both the distal frame 14 and the proximal frame 12 may be made, at least in part, from Nitinol, stainless steel, or bio-absorbable or non-bio-absorbable polymers.

Figure 2A:
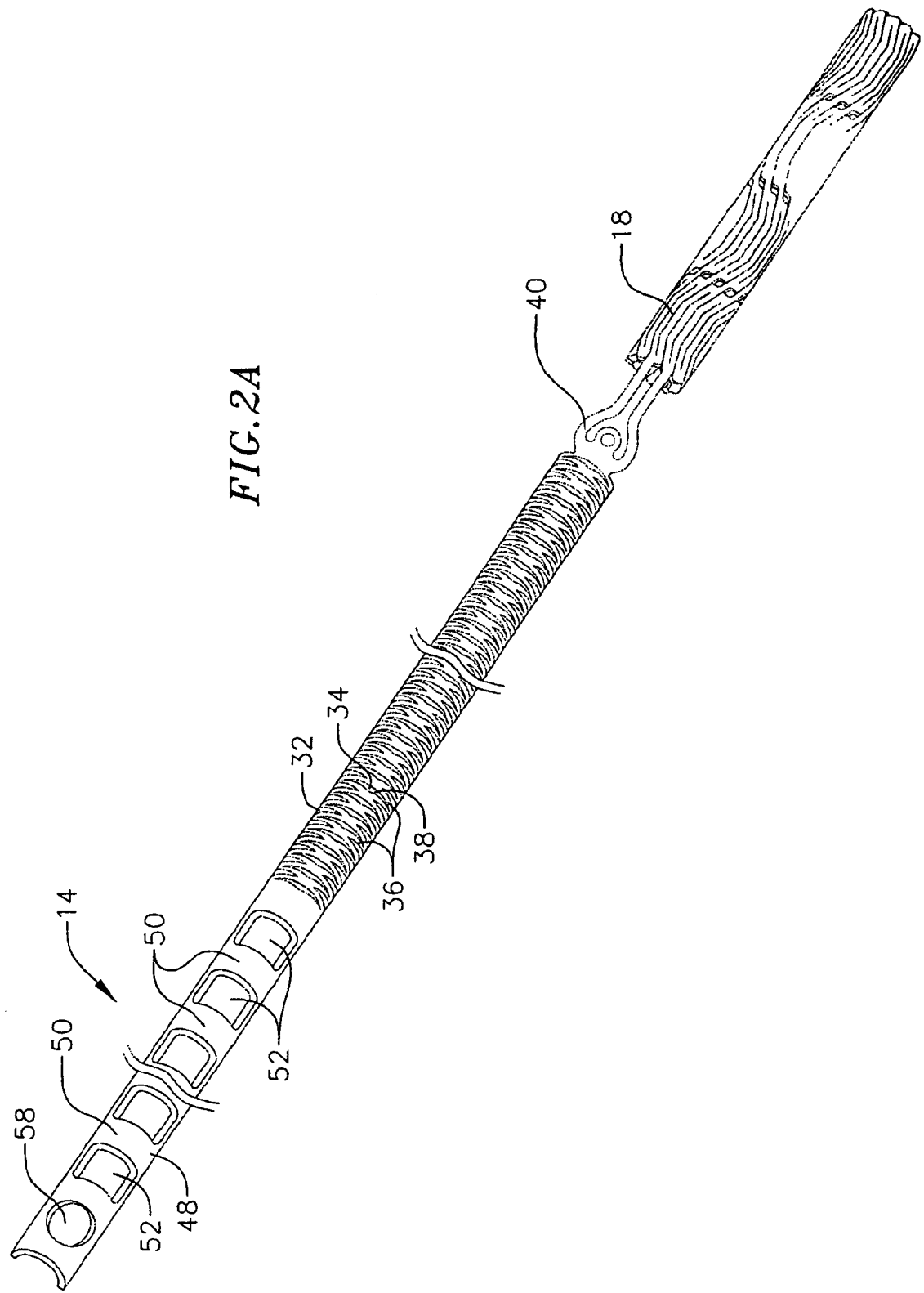
FIG. 2a is a side view of an embodiment of a distal frame of the present invention.

With reference to FIG. 2a, the distal frame 14 is shown in isolation wherein the distal anchor 18 is in a compressed state. However, the distal anchor also has an expanded state. In the compressed state, the distal anchor 18 has a diameter that is less than the diameter of the coronary sinus 20. In the expanded state, the distal anchor 18 has a diameter that is equal to or greater than the diameter of the coronary sinus 20. In one embodiment, the distal anchor 18 is a self-expandable stent made from a shape memory material, such as, for example, Nitinol. The stent has a mesh structure such that in its expanded state, the stent provides temporary resistance to axial movement within the coronary sinus 20 and further allows the walls of the coronary sinus to grow around the stent to more permanently anchor the stent in place.

Figure 5B:
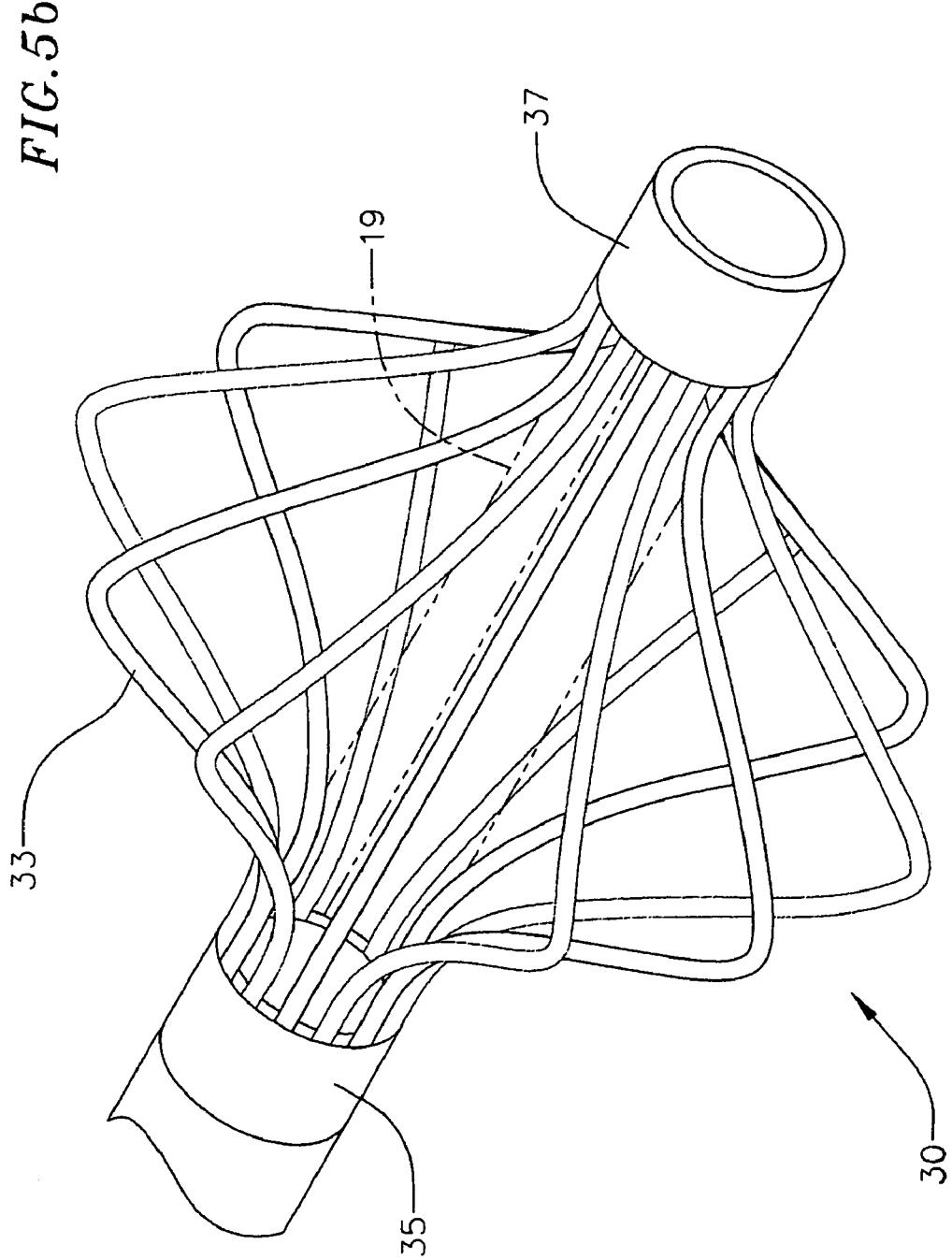
FIG. 5b is a perspective view of the anchor of FIG. 5a in an expanded state.

With reference to FIGS. 5a and 5b, an alternative embodiment is illustrated wherein the distal anchor takes the form of a basket 30. The basket 30 has two states, a compressed state and an expanded state. In the compressed state, the basket 30 is insertable into the coronary sinus or other coronary vessel. More specifically, as shown in FIG. 5a, in the compressed state, the basket 30 is substantially cylindrical and includes a plurality of strands 33 extending longitudinally from a proximal end 35 to a distal end 37 of the basket spaced evenly around the basket's circumference. The proximal end 35 of the basket 30 may be fixedly attached to the distal frame 14 by an adhesive. The distal end 37 of the basket 30 is fixedly attached to an inner tube 19 which telescopes with the distal frame. As shown in FIG. 5b, in the expanded state, the basket 30 is sized for securement to an inner wall of the coronary sinus 20. More specifically, in the expanded state, wherein the distance between the proximal end 35 and the distal end 37 of the basket 30 is decreased due to proximal movement of the inner tube 19, the strands 33 may form substantially triangular shapes with the apex of the triangle protruding away from the center of the basket for engagement with the inner wall. In another preferred embodiment, the strands 33 are made from a shape memory material (e.g. Nitinol) allowing the basket 30 to transform from its compressed state to its expanded state by the retraction of a delivery sheath or other compression member.

Although the distal anchor 18 is described above as taking the form of a self-expandable stent or basket 30, any anchoring member capable of engaging the inner wall of the coronary sinus may be used. For example, the distal anchor 18 may be a balloon expandable stent or any other type of expandable stent. Additionally, the distal anchor 18 may be a balloon adapted to anchor the distal frame 14 in the coronary sinus 20, for instance, by having a textured outer surface. Further, the distal anchor 18 may also include hooks, barbs or a biocompatible adhesive to further aid the anchor in maintaining attachment to a vessel wall in the expanded state.

Referring now to FIGS. 2a and 2c, proximally adjacent to the distal anchor 18 is a bridge 32 having a semi-cylindrical cross-section. In one embodiment, the bridge 32 is made from Nitinol and is sufficiently flexible to allow the bridge to conform to the shape of the coronary sinus 20. In the illustrated embodiment, the bridge 32 comprises a series of flexible members in the form of X-shaped elements 36. In the illustrated embodiment, each X-shaped element is connected to an adjacent X-shaped element, thereby allowing a space 38 to be created between adjacent X-shaped elements. FIG. 2c illustrates the bridge 32 laid flat for purposes of illustration. However, as shown in FIG. 2a, the bridge 32 is preferably bent about the longitudinal axis to form a semi-cylindrical shape which minimizes the chances that a sharp edge of the bridge will puncture or damage a portion of the coronary sinus during insertion of the device. In other embodiments, the bridge may have other cross-sectional shapes, such as, for example, a tubular shape.

In still other embodiments, a bio-absorbable or decomposable material (not shown) may be disposed within the spaces 38 between the X-shaped elements 36. The material may be selected such that it is absorbed or decomposes over a substantial period of time. The material in the spaces initially maintains the elongate body in an extended condition. However, as the material absorbs or decomposes, the X-shaped elements may deform such that the width of the spaces decrease, thereby causing the elongate body to further reduce in length after deployment in the body. In this embodiment, the bridge and X-shaped elements are preferably formed of a shape memory material. The combination of a shape memory material with an absorbable or decomposable material advantageously allows the proximal and distal anchors 16, 18 to more securely attach to the inner wall of the vessel before the elongate body reshapes the coronary sinus and mitral valve. This feature also allows the body to adjust to the reshaping of the mitral valve in a more gradual manner. Additional details regarding preferred embodiments of an elongate body comprising bio-absorbable and/or decomposable materials disposed along a bridge portion may be found in Applicant's co-pending U.S. application Ser. No. 11/014,273, filed Dec. 15, 2004, which is incorporated by reference herein.

With reference again to the embodiment shown in FIGS. 2a and 2c, the bridge 32 is connected to the distal anchor 18 by a link 40. More specifically, the link 40 has a base 42 and arms 44 that extend from the base and which are connected to the distal anchor 18. However, the bridge 32 may be connected to the distal anchor 18 by any appropriate means which provides a flexible yet structurally reliable connection.

With particular reference to FIG. 2a, a ratcheting strip 48 is located proximal to the bridge 32 on the distal frame 14. In one preferred embodiment, the ratcheting strip includes an alternating series of engagement portions 50 and openings 52. As will be described in more detail below with reference to FIG. 3, the openings 52 are adapted to receive a latch 54 from an accepting member 56 located on the proximal frame. The engagement portions 50, which may be, for example, bumps or barbs, are preferably spaced about 2-4 mm apart from each other. The specific shape of the engagement portions 50 and the openings 52 is not critical as long as the ratcheting strip 48 allows the accepting member 56 to become slidably connected to the ratcheting strip. Similar to the bridge 32, the ratcheting strip 48 preferably has a semi-cylindrical cross-section such that it does not puncture or otherwise damage the coronary sinus 20. However, in alternative embodiments, the ratcheting strip 48 may have a tubular or a flat configuration.

With reference to FIGS. 2a and 2b, at a proximal end of the ratcheting strip 48 is a hole 58 which serves to receive an actuating member 60. As shown in FIG. 2b, the actuating member 60 may take the form of a wire or other elongate member having a hook-shaped distal end 61 which is adapted to fit into the hole 58 on the ratcheting strip 48. When the actuating member 60 is engaged with the hole 58 (see FIG. 8), the actuating member 60 may be used to move the distal frame 14 relative to the proximal frame 12 for adjusting the length of the elongate body. Although a particular actuating member is illustrated for fitting into a hole in the distal frame, a wide variety of alternative actuating mechanisms may be used for releasably engaging the distal frame.

With reference now to FIG. 3, the proximal anchor 16 on the proximal frame 12 serves to anchor the proximal frame to the coronary sinus 20. Similar to the distal anchor 18, the proximal anchor 16 has two states, a compressed state and an expanded state. In the compressed state, the proximal anchor 16 has a diameter that is less than the diameter of the coronary sinus 20. In the expanded state, the proximal anchor 16 has a diameter that is equal to or greater than the diameter of the coronary sinus 20. In one preferred embodiment, the proximal anchor 16 is a self-expandable stent made from Nitinol. The stent has a structure such that, in its expanded state, provides temporary resistance to axial movement within the coronary sinus 20 and further allows the walls of the coronary sinus to grow around the stent to more permanently anchor the stent in place. As described above with respect to the distal anchor 18, the proximal anchor 16 may also be a basket, a balloon inflated stent, a balloon or any other appropriate anchor. Also as described above, the proximal anchor 16 may include barbs, hooks or a biocompatible adhesive to help maintain its attachment to a vessel in the expanded state.

Figure 4:
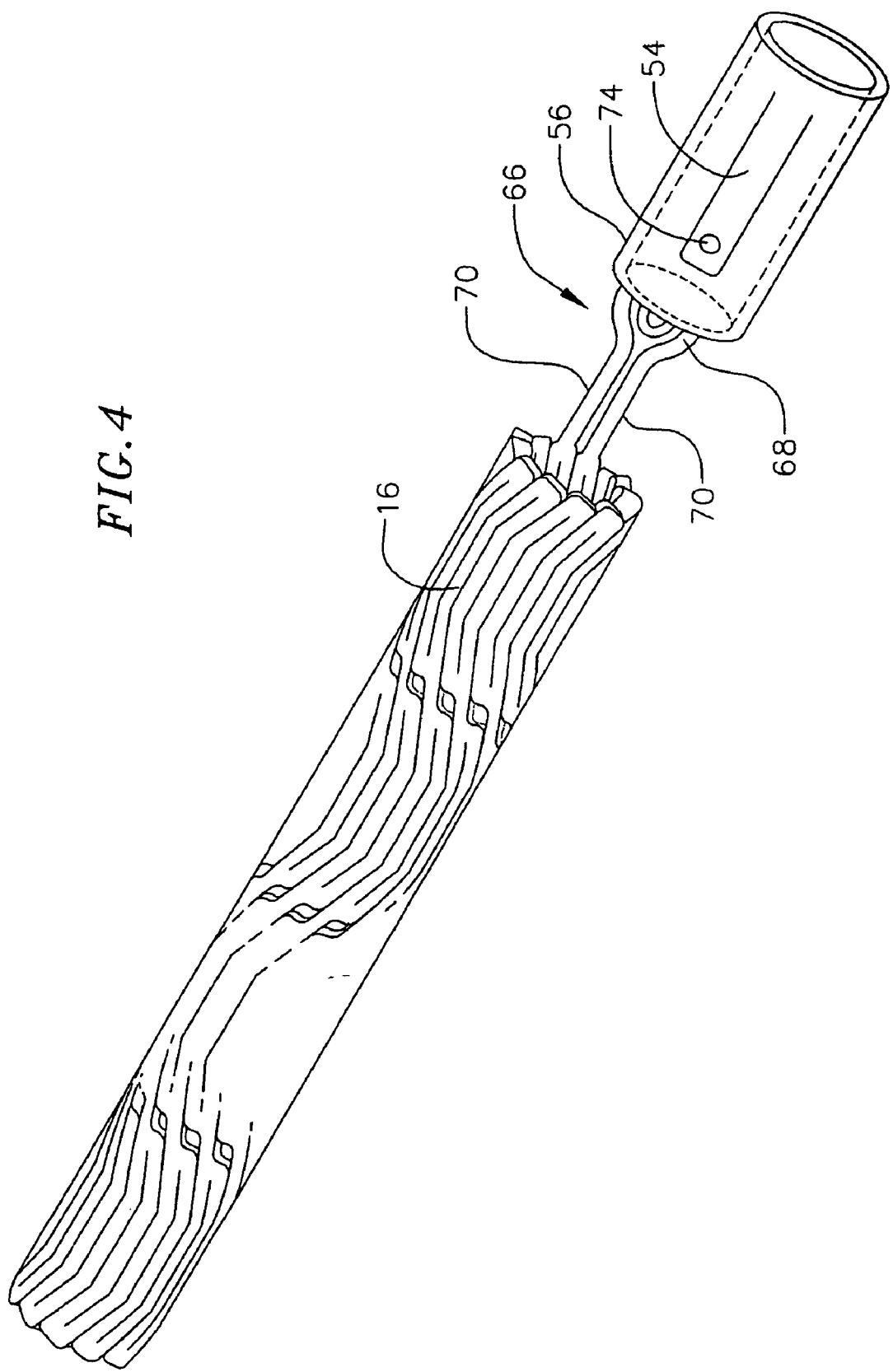
FIG. 4 is a top view of an embodiment of a proximal frame of the present invention.

The accepting member 56 is preferably located distally from the proximal anchor 16 on the proximal frame 12. In the illustrated embodiment, the accepting member 56 is cylindrically shaped and is substantially the same diameter as the proximal anchor 16 when the proximal anchor is in the compressed state. However, the accepting member 56 may be any shape suitable for receiving the ratcheting strip 48 of the distal frame 14. For example, the accepting member may be semi-cylindrical or rectangular. The accepting member 56 has a resilient latch 54 which is preferably biased to protrude at an angle toward the center of the accepting member. The latch 54 is adapted to fit into the openings 52 of the ratcheting strip 48 when the proximal frame 12 engages the distal frame 14 as is described in more detail below. As shown in FIG. 4, the latch 54 further includes a hole 74 to which a release mechanism may be attached to disengage the latch from the ratcheting strip 48 as described in more detail below.

With reference now to FIG. 4, it can be seen that the accepting member 56 is preferably attached to the proximal anchor 16 by a link 66. Similar to the link 40 described above, the link 66 has a base 68 and arms 70 that extend from the base and which are connected to the proximal anchor 16. However, the accepting member 56 may also be attached to the proximal anchor 16 by any appropriate means which provides a flexible yet structurally reliable connection such as by being thermally or adhesively bonded.

With reference now to FIGS. 6 and 7, the elongate body 10 is illustrated with the proximal and distal frames 12, 14 connected to form a telescoping member. More specifically, the distal frame 14, which has a smaller diameter than the proximal frame 12, is inserted into the distal end of the proximal frame. Once the latch 54 has encountered the first space 52 on the ratcheting strip 48, the latch will act as a lock to keep the distal frame 14 attached to the proximal frame 12. Additionally, the effective length of the elongate body 10 (i.e. the distance between the proximal anchor 16 and the distal anchor 18) may be changed by pulling the distal frame 12 such that the distal anchor moves proximally toward the proximal anchor. As the distal frame 12 is pulled proximally, such as by using the actuating member 60, the latch 54 acts as a ratchet. More particularly, the latch is forced around each successive engagement portion 50 and engages each successive opening 58, thereby shortening the length of the elongate body 10, as shown in FIG. 7.

Figure 10:
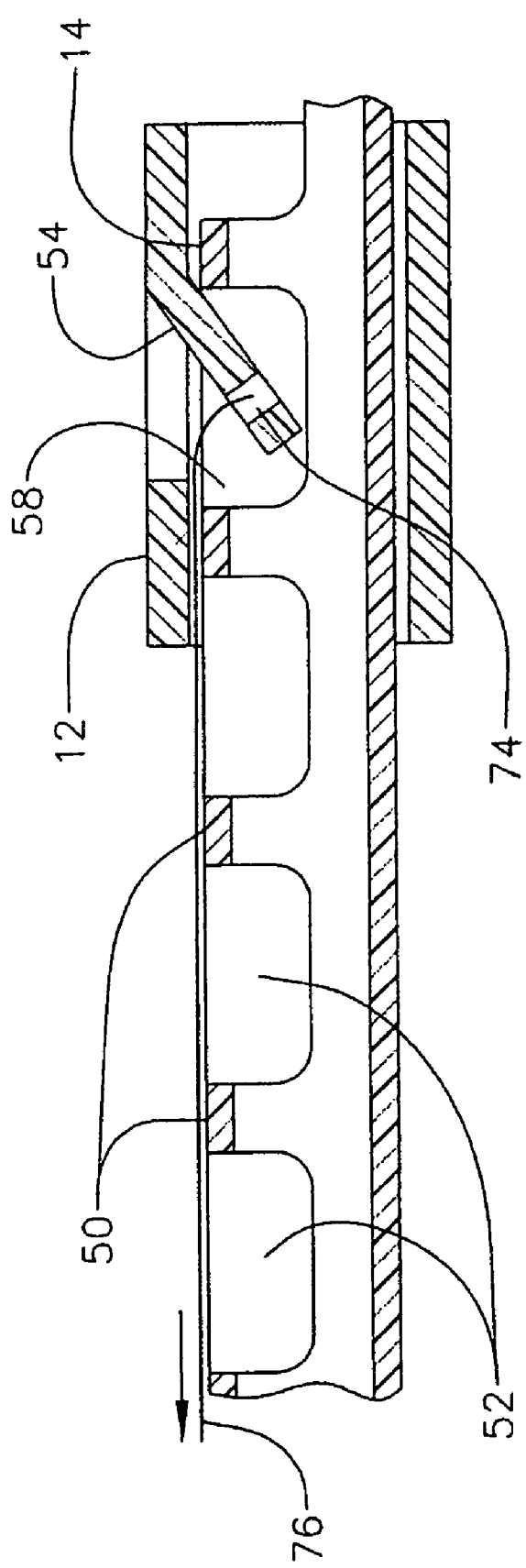
FIG. 10 is a schematic detail of a release mechanism embodiment of the present invention.

If the elongate body 10 needs to be lengthened, a release mechanism may be provided for releasing the proximal frame 12 from the distal frame 14. One exemplary embodiment of a release mechanism is shown schematically in FIG. 10. More specifically, a release wire 76 attached through the hole 74 on the latch 54 is pulled proximally, causing the latch to pivot outward and disengage from the opening 58, thereby allowing the proximal frame 12 to be slid apart from the distal frame 14. Once the proximal frame 12 and the distal frame 14 have been situated at the desired position, the release wire 76 may be released allowing the latch to again engage in an opening 58 of the ratcheting strip 48.

With reference now to FIGS. 1 through 10, one preferred method of using the elongate body 10 will now be described in more detail. First, a guidewire (not shown) is inserted into the coronary sinus 20. The elongate body 10 is then mounted onto a delivery catheter covered by a delivery sheath as is known in the art and inserted into the coronary sinus 20 over the guidewire. The delivery sheath 80 (FIG. 6) serves to keep the proximal and distal anchors in their compressed state. The actuating member 60 and release wire 76 (if necessary) extend through the coronary sinus 20 and out of the patient's body such that they may be manipulated by a clinician.

Figure 8:
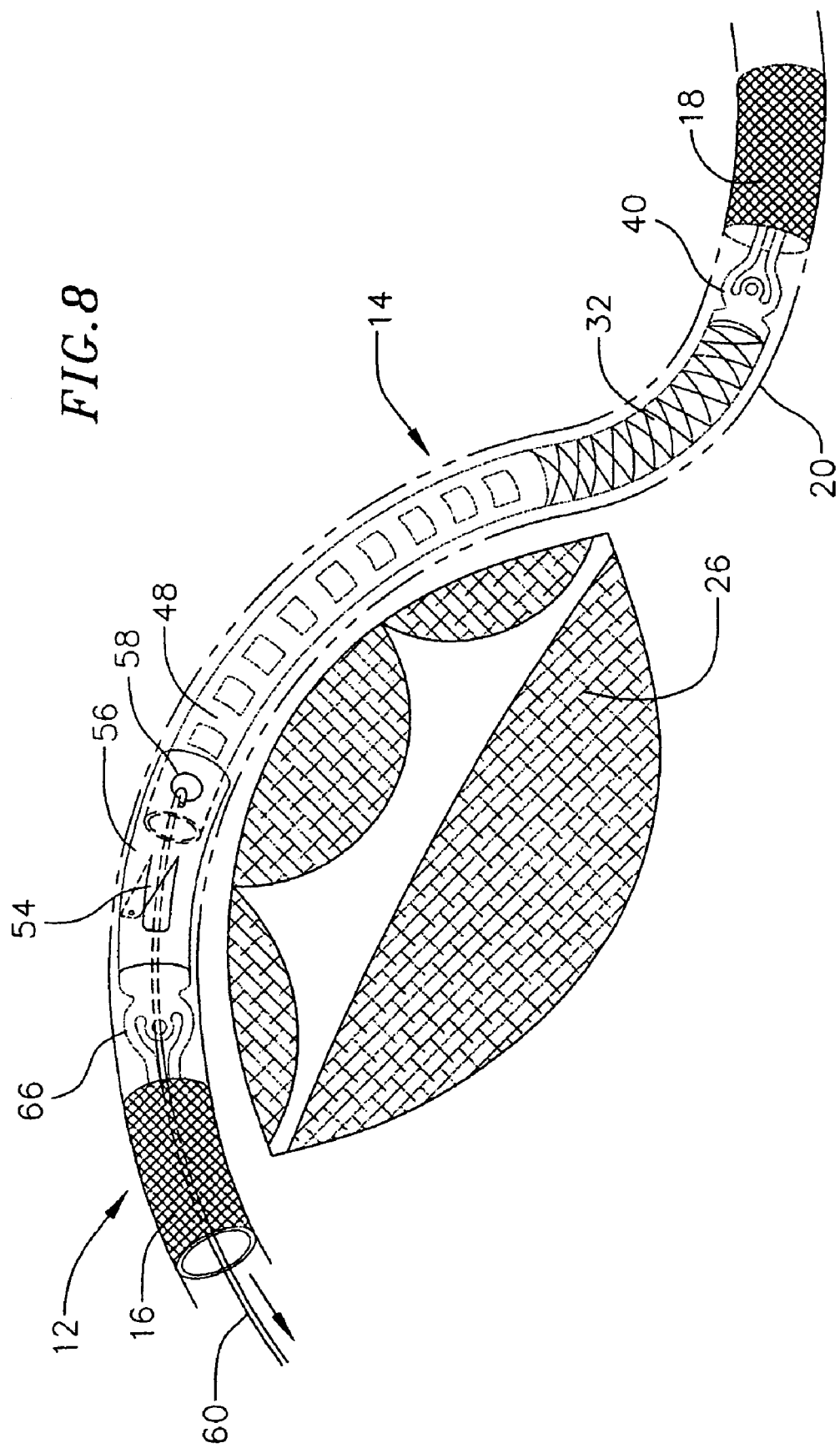
FIG. 8 is a schematic side view of an elongate body of the present invention in an extended state in the coronary sinus including the distal frame and proximal frame.

With particular reference to FIG. 8, the elongate body 10 including the proximal frame 12 and the distal frame 14 is initially inserted into the coronary sinus 20. Specifically, the elongate body 10 is inserted into the part of the coronary sinus known as the great cardiac vein and if desired, the device is inserted all the way to the anterior interventricular vein. Once the distal frame 14, and more specifically, the distal anchor 18, has been placed in a desired position in the coronary sinus 20, the distal anchor is transformed from its compressed state into its expanded state by retraction of the delivery sheath 80 (FIG. 6). The expansion of the distal anchor 18 allows the anchor to be pressed against the inner walls of the coronary sinus 20 and become anchored there. A more permanent anchoring occurs over time as the vessel wall grows around the anchor and allows the anchor to become part of the coronary sinus itself.

Once the distal anchor 18 has been expanded such that the anchor is in contact with the inner walls of the coronary sinus 20, the proximal anchor 16 is preferably positioned so that its proximal end is at or adjacent the ostium 24 and within the coronary sinus 20. Then the delivery sheath 80 (FIG. 6) is pulled further proximally such that the proximal anchor 16 is released from within the delivery sheath and transformed from its compressed state to its expanded state. As with the distal anchor 18, the expansion of the proximal anchor 16 allows the anchor to be pressed against the inner walls of the coronary sinus 20 and become anchored there. In one exemplary embodiment, the expanded diameter of the proximal stent may be substantially larger, for example about 5-8 times larger, than the expanded diameter of the distal stent.

Figure 9:
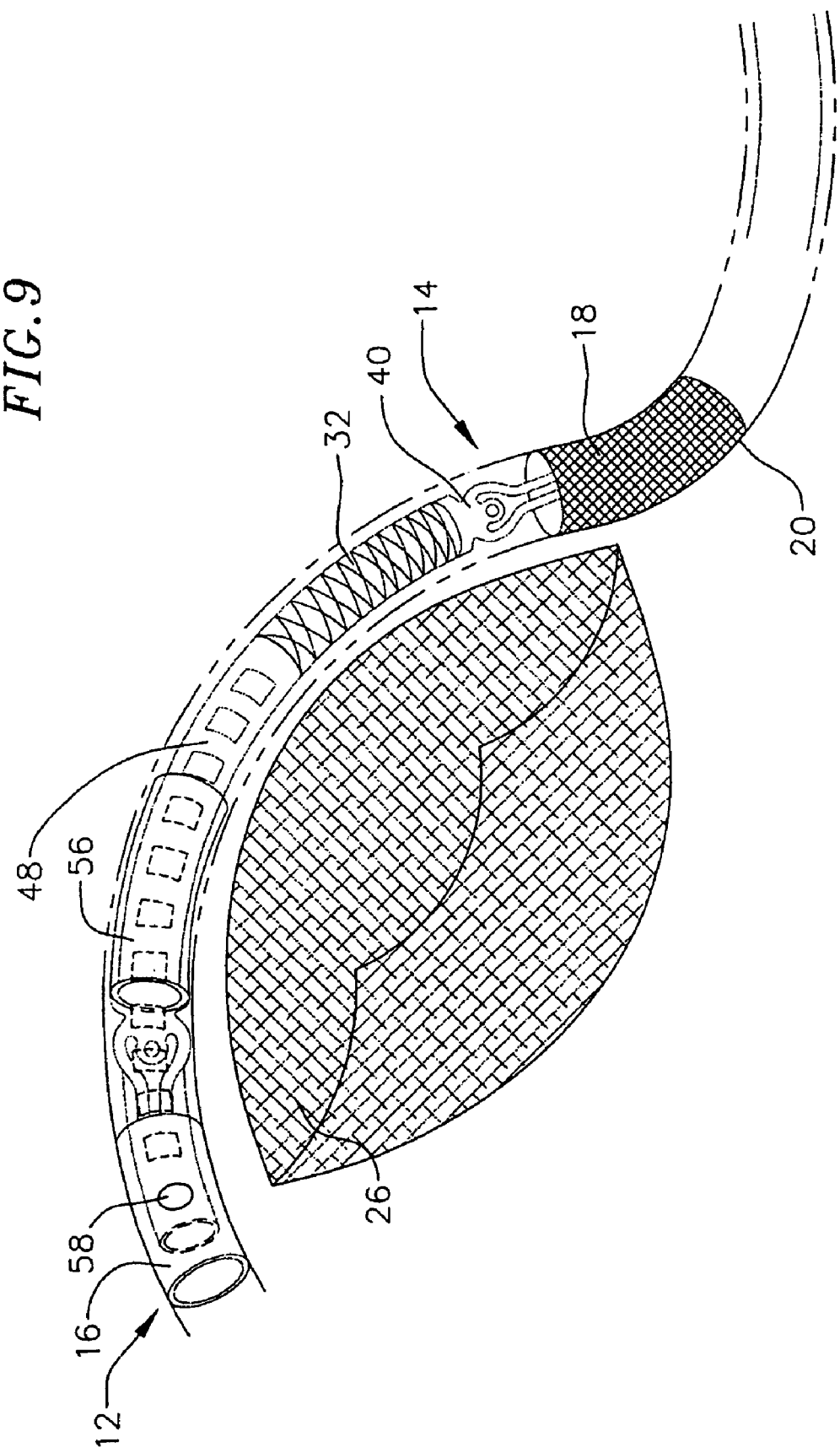
FIG. 9 is a schematic side view of an elongate body of the present invention in a contracted state in the coronary sinus including the distal frame and proximal frame.

With reference now to FIG. 9, once both the proximal anchor 16 and the distal anchor 18 have been transformed from their compressed state into their expanded state and both anchors have anchored the elongate body 10 into the coronary sinus, the actuating member 60 is used to pull the distal frame 14 proximally. Pulling the distal frame 14 proximally will have at least one of two effects on the coronary sinus 20. First, pulling the distal frame 14 proximally may shorten the distance between the distal anchor 18 and the proximal anchor 16 as by pinching the opposite ends of the coronary sinus together, thereby causing a decrease of the radius of curvature of the coronary sinus 20. Decreasing the radius of curvature of the coronary sinus 20 causes a decrease in the anterior-posterior (A-P) distance of the mitral valve 26 and causes a decrease in the P1-P3 distance. Second, pulling the distal frame 14 proximally may shorten the distance between the distal anchor 18 and the proximal anchor 16 along the length of the coronary sinus 20 to cinch the coronary sinus tighter around the mitral valve 26, also decreasing the A-P distance and decreasing the P1-P3 distance of the mitral valve. This change in the shape of the mitral valve 26 allows the gap between the anterior leaflet 29 and the posterior leaflet 31 causing mitral regurgitation to close, thus decreasing or eliminating mitral regurgitation. Once the elongate body 10 has been adjusted to a desired length, the actuating member 60 is disengaged from the proximal frame 12 and removed from the patient's body.

In an alternate embodiment, after both the proximal anchor 16 and the distal anchor 18 have been transformed from their compressed state into their expanded state and both anchors have anchored the elongate body 10 into the coronary sinus 20, a catheter (not shown) is inserted through the expanded proximal anchor 16 and over the actuating member 60 so that a distal end of the catheter abuts the accepting member 56. The actuating member 60 is then used to pull the distal anchor 18 proximally. The guide catheter serves to provide a counter force to hold the accepting member 56 more securely in place as the actuating member 60 is pulled.

If the effective length of the elongate body 10 is found to be too short, the latch 54 may be released as described above and the distance between the proximal anchor 12 and the distal anchor 18 may be increased by using the actuating member 60 to push the distal frame 14 distally. Alternatively, the distal frame may be pushed distally by using the inherent elastic force of the heart tissue. The procedure for adjusting the length of the elongate body 10 may be repeated as many times as necessary to achieve the desired length. Additionally, the modification in length of the elongate body 10 does not have to occur during a single procedure. In preferred embodiments, the length of the elongate body 10 may be adjusted even after a period of hours, weeks, or months have passed.

When the ratcheting strip 48 is pulled through the proximal frame 12 and the accepting member 56, a considerable length of the ratcheting strip may extend throughout the coronary sinus 20 and into the right atrium 22. The ratcheting strip 48 may therefore have two sections where the strip is held together by a screw mechanism, one with threads winding clockwise and another with the threads winding counterclockwise. Thereby the protruding ratcheting strip 48 may be detached at two different sites, depending upon turning the actuating member 60 clockwise or counterclockwise. Additionally, in an alternate embodiment, the arms 44 of the link 40 of the distal frame 14 may be of a length such that when the ratcheting strip 48 is pulled proximally, the ratcheting strip 48 does not extend into the right atrium 22.

Figure 11:
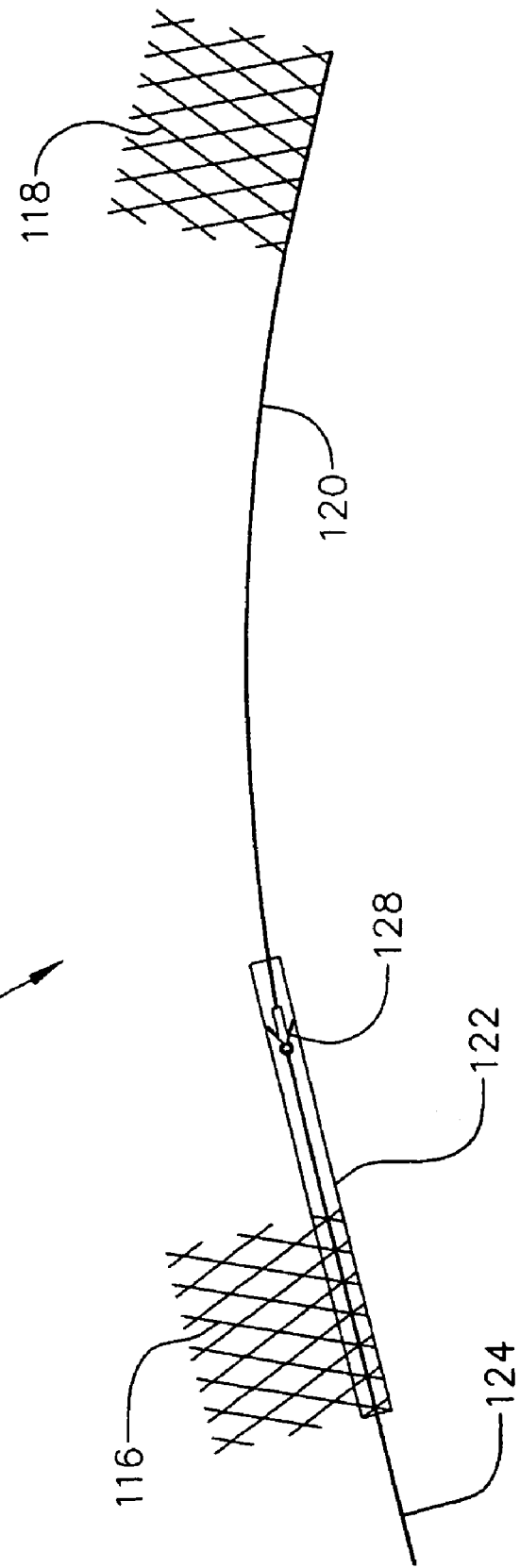
FIG. 11 is a side view of an alternate embodiment of an elongate body of the present invention.

With reference now to FIG. 11, a first alternative embodiment of the present invention includes an elongate body 110 comprising a distal anchor 118, a proximal anchor 116, a locking shaft 122 attached to the proximal anchor, and a locking pin 128. As described above with respect to the previous embodiment, the distal anchor 118 and the proximal anchor 116 have two states, a compressed state and an expanded state. In the compressed state, the anchors 116, 118 have a diameter that is less than the diameter of the coronary sinus 20. In the expanded state, the anchors 116, 118 have a diameter that is equal to or greater than the diameter of the coronary sinus 20.

The proximal anchor 116 and the distal anchor 118 are preferably self-expandable stents made from Nitinol. The stents have a structure such that in their expanded state, the stents provide temporary resistance to movement within the coronary sinus 20 and further allow the walls of the coronary sinus to grow around the stents to more permanently anchor the stents in place.

A cinching thread 120 is attached to the distal stent 118. The cinching thread is an elongate member preferably in the form of a flexible wire made from Nitinol or a monofilament. The flexible wire is of a sufficient length to extend the entire length of the coronary sinus 20. Alternatively, the cinching thread may also be a rod, wire, or the like, and it may have varied shapes, such as a zig-zag or X-shaped elements.

Figure 12:
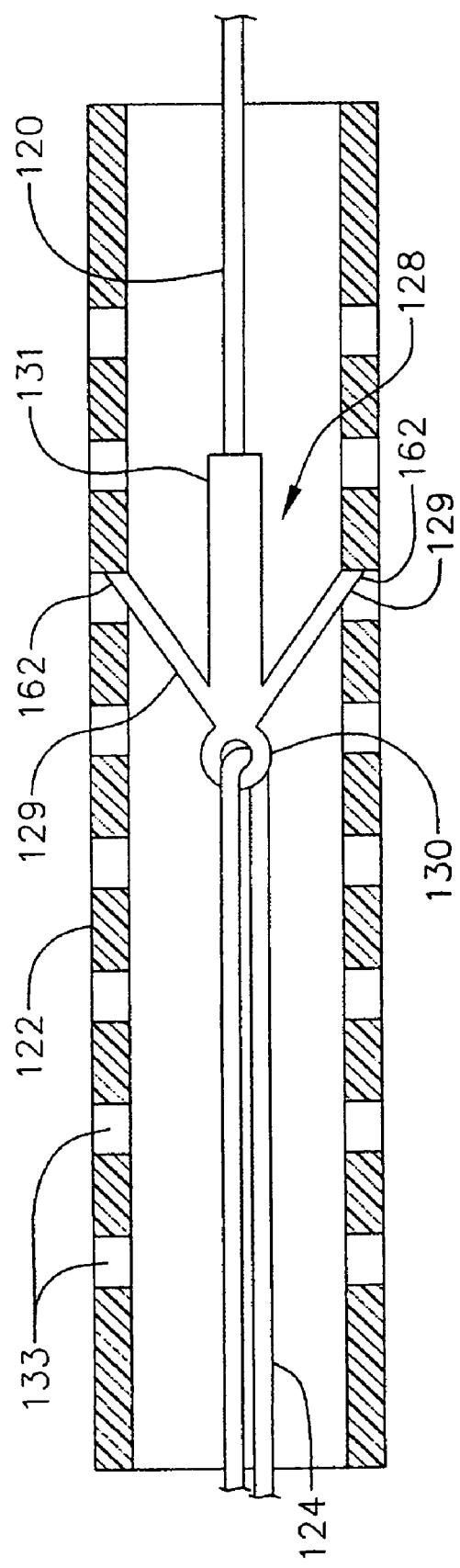
FIG. 12 is a side view of a locking mechanism of the present invention including a locking pin.

With reference to FIG. 12, the locking pin 128 is attached to a proximal end of the cinching thread 120. The locking pin 128 is preferably made from Nitinol and includes a cylindrical body 131, two resilient arms 129 extending from the body and a head 130 at a proximal end of the body. The resilient arms 129 are attached to the body 131 distally adjacent to the head 130 and extend distally at an angle. The locking pin 128 has an open position and a closed position. In the open position, ends 162 of the arms 129 of the locking pin 128 are separated by a distance that is about equal to or greater than the inner diameter of the locking shaft 122, as best shown in FIG. 12. In the closed position, the ends 162 of the arms 129 are separated by a distance that is less than the inner diameter of the locking shaft 122. The head 130 of the locking pin 128 is a loop into which a pull line 124 is inserted. The pull line 124 is used to pull the locking pin 128 through the flexible locking shaft 122 as is described in greater detail below. The locking pin 128 embodiment described herein has been found to be particularly effective. However, it will be appreciated that a variety of alternative resilient members, one of which being described below, may be substituted for the locking pin.

The flexible locking shaft 122 is also preferably made from Nitinol and is attached to the proximal stent 116. In one example, the locking shaft 122 may be welded to the proximal anchor or, in another example, may be machined as a single piece along with the stent 116. Additionally, the locking shaft 122 may also includes hooks or barbs. The locking shaft 122 is a cylindrical tube having openings 133 evenly spaced on opposite sides of the shaft. The openings 133 are adapted to receive the arms 129 of the locking pin 128.

Figure 13:
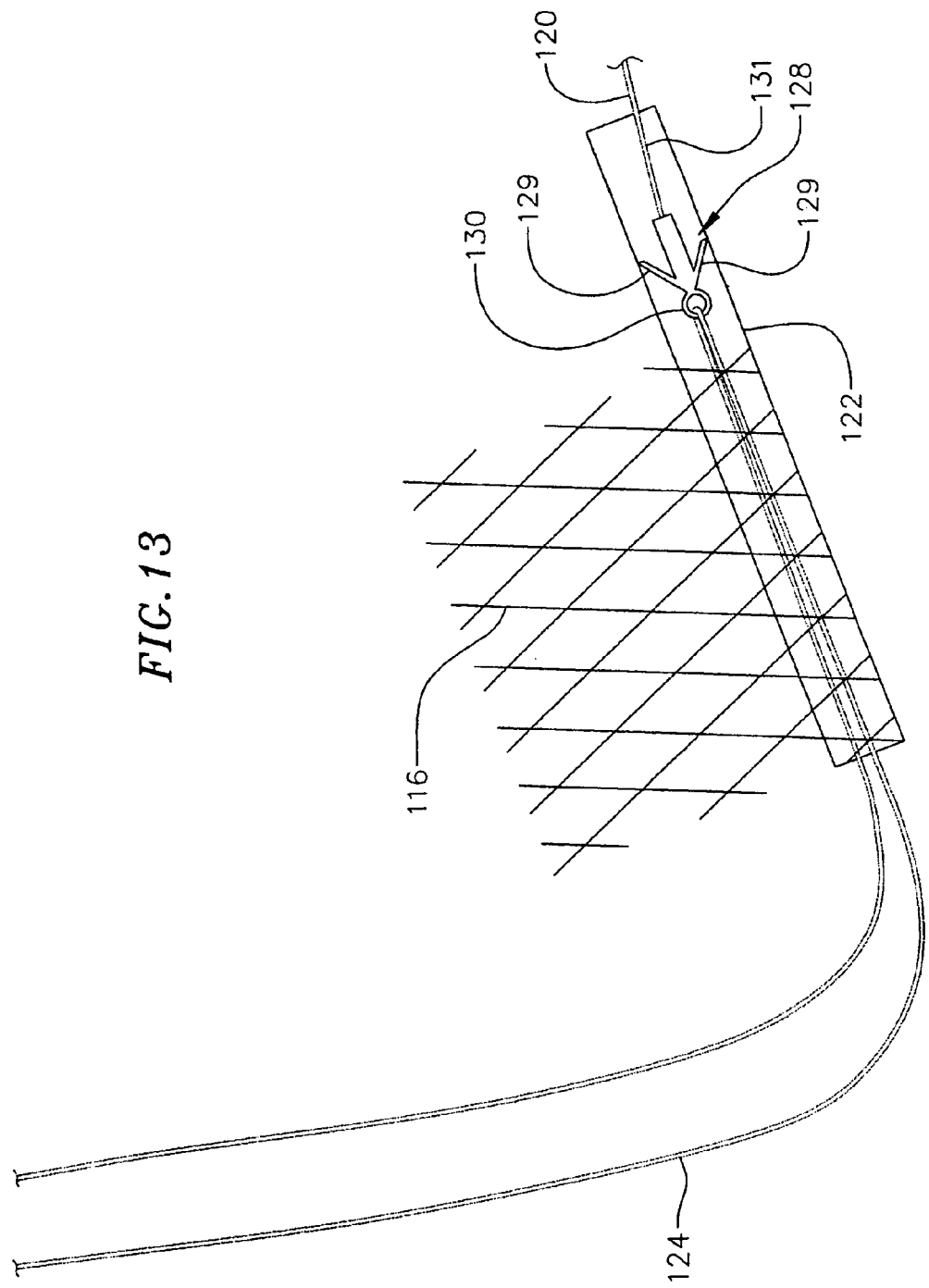
FIG. 13 is a side view of a proximal end of the elongate body of FIG. 11 including a pull line.

As partially shown in FIG. 13, the pull line 124 is preferably looped through the head 130 of the locking pin 128 and extends through the coronary sinus 20, through the jugular vein and out of the patient's body where it can be manipulated by an attendant. When the pull line 124 is pulled proximally, the locking pin 128, cinching thread 120 and distal stent 118 are also pulled proximally. As the locking pin 128 passes through the locking shaft 122, the arms 129 of the locking pin, acting as a ratchet, engage each successive opening 133 of the shaft as shown in FIG. 12. The structure of the locking pin 128 is such that it may be pulled proximally, but without the aid of a release device such as a release catheter described below, it will not move distally.

Figures 14A, 14B:
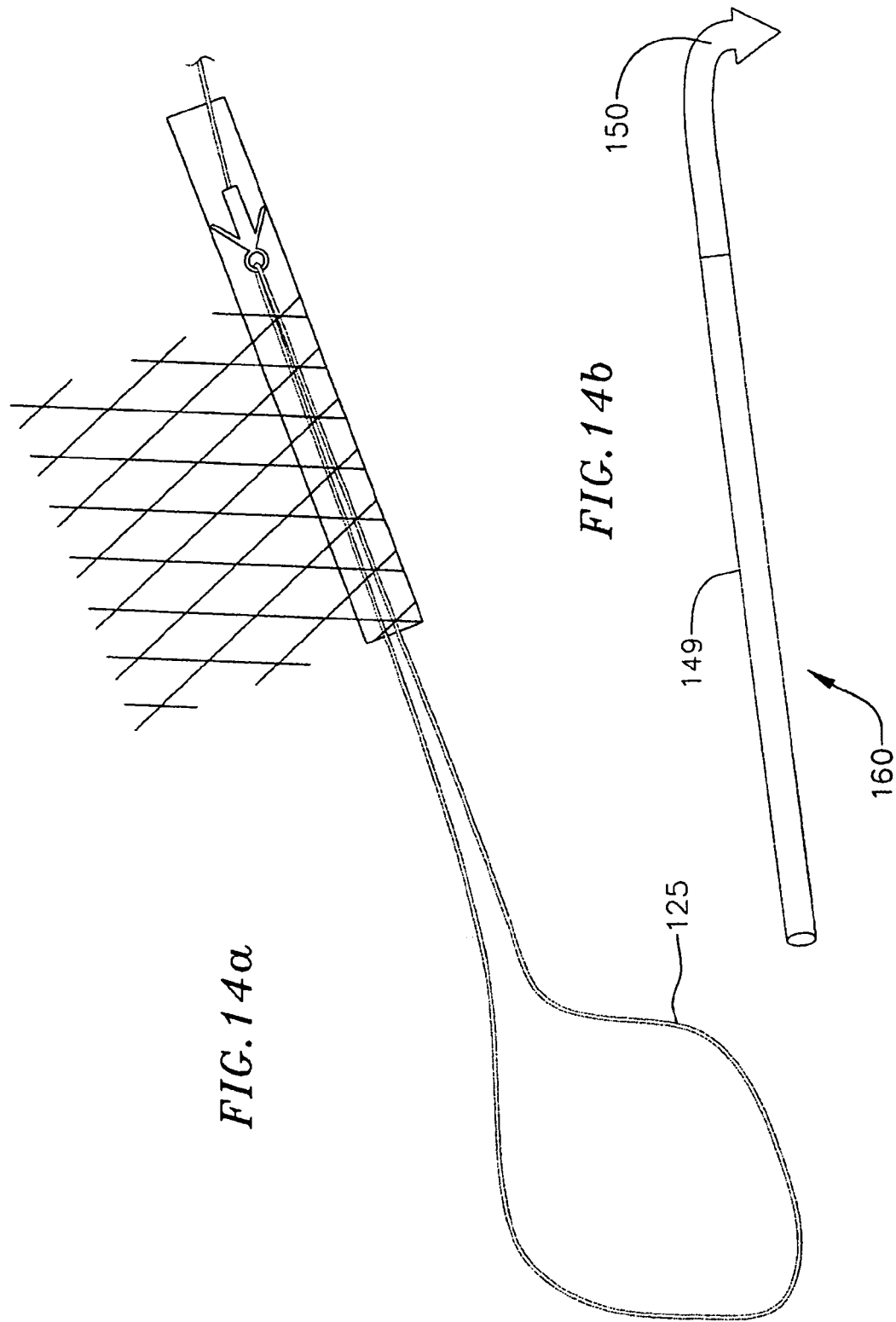

With reference to FIG. 14a, in one alternative embodiment, the pull wire includes a pull loop 125. Rather than extending out of a patient's body, the pull loop may remain within the patient's vascular system, preferably in the right atrium, and may be pulled proximally with an actuating member 160 as shown in FIG. 14b or any other grasping means used in interventional vascular procedures, such as pliers. The actuating member includes a body 149 made from a flexible biocompatible material and a hook-shaped distal end 150 which is used to snare the pull loop 125 and pull it proximally.

In another alternative embodiment, the pull loop 125 may also be provided with x-ray (radiopaque) markers (not shown) that allow the loop to be seen on a screen which aids an attendant in finding the loop in the patient's vascular system. Further, the loop 125 may be made from an absorbable material which will be absorbed by the body over time, allowing the loop to be a temporary adjustment means for the elongate body 110.

The elongate body 110 may be deployed as follows. First, a guidewire (not shown) is inserted into the coronary sinus 20, the great cardiac vein and extending into the interventricular vein of the heart. The elongate body is then mounted onto a delivery catheter 178, covered by a delivery sheath and inserted into the coronary sinus 20 over the guidewire. The pull wire 124 extends through the coronary sinus 20 and out of the patient's body such that the pull wire may be manipulated by an attendant.

When initially inserted into a patient, the elongate body 110 including the proximal anchor 116 and the distal anchor 118 is inserted into the coronary sinus 20 as distally as possible. Specifically, the elongate body 110 may be inserted into the part of the coronary sinus known as the great cardiac vein.

Once the distal anchor 118 has been placed in a desired position in the coronary sinus 20, the distal anchor is transformed from its compressed state into its expanded state by retraction of the delivery sheath. The expansion of the distal anchor 118 allows it to be pressed against the inner walls of the coronary sinus 20 and become anchored there. A more permanent anchoring occurs over time as the vessel wall grows around the anchor and allows the anchor to become a part of the coronary sinus itself.

Once the distal anchor 118 has been expanded such that the anchor is in contact with the inner walls of the coronary sinus 20, the delivery sheath is pulled further proximally such that the proximal anchor 116 is released from the delivery sheath and transformed from its compressed state to its expanded state. As with the distal anchor 118, the expansion of the proximal anchor 116 allows the anchor to be pressed against the inner walls of the coronary sinus 20 and become anchored there. In one exemplary embodiment, the expanded diameter of the proximal stent is about 5-8 times larger than the expanded diameter of the distal stent. A more permanent anchoring occurs over time when the vessel wall grows around the anchor and allows the anchor to become part of the coronary sinus itself.

Figure 15:
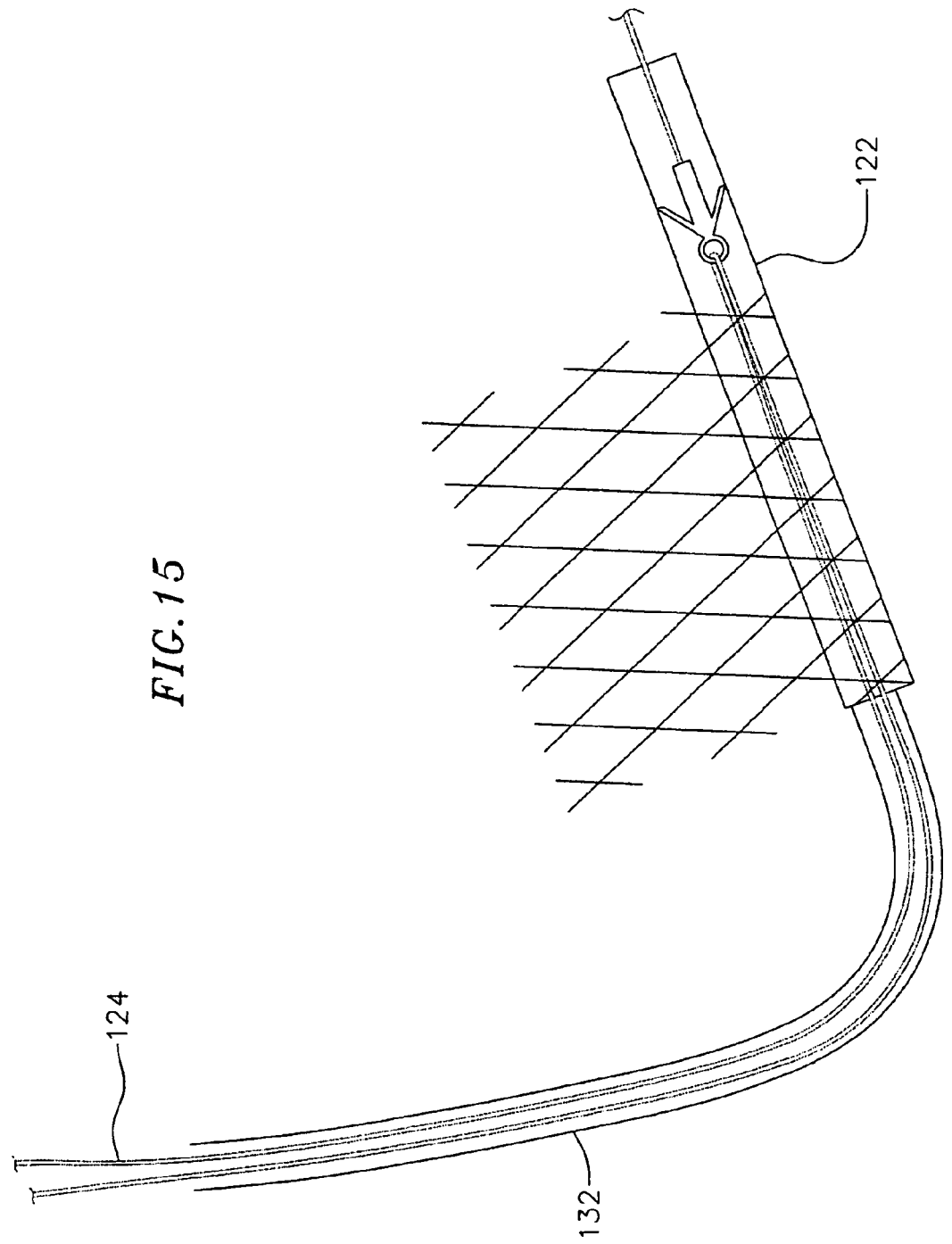
FIG. 15 is a side view of a proximal end of the elongate body of FIG. 11 including a guide catheter.

After both the proximal anchor 116 and the distal anchor 118 have been transformed from their compressed state into their expanded state and both anchors have anchored the elongate body 110 into the coronary sinus, a guide catheter 132 is inserted over the pull line 124 so that a distal end of the catheter abuts the locking shaft 122 as shown in FIG. 15. The pull wire 124 is then used to pull the distal anchor 118 proximally. The guide catheter 132 serves to provide a counter force to hold the locking shaft 122 more securely in place as the pulling force is applied to the pull wire 124.

Pulling the distal anchor 118 proximally will have at least one of two effects on the coronary sinus 20. First, pulling the distal anchor 118 proximally may shorten the distance between the distal anchor 118 and the proximal anchor 116 as by pinching the opposite sides of the coronary sinus 20 together, causing a decrease of the radius of curvature of the coronary sinus. Decreasing the radius of curvature of the coronary sinus 20 causes a decrease in the anterior-posterior (A-P) distance of the mitral valve 26 and causes an decrease in the P1-P3 distance. Second, pulling the distal anchor 118 proximally may shorten the distance between the distal anchor 118 and the proximal anchor 116 along the length of the coronary sinus 20 to cinch the coronary sinus tighter around the mitral valve 26, also decreasing the A-P distance and decreasing the P1-P3 distance of the mitral valve. This change in the shape of the mitral valve 26 allows the gap between the anterior leaflet 29 and the posterior leaflet 31 causing mitral regurgitation to close, thus decreasing or eliminating mitral regurgitation. Once the elongate body 110 has been adjusted to a desired length, one end of pull wire 124 is released and pulled through the hole in the head 130 of the locking pin 128 to disengage it therefrom and removed from the patient's body.

If the effective length of the elongate body 110 (i.e. the distance between the proximal anchor 116 and the distal anchor 118) is found to be too short, a release catheter 134 may be inserted into the locking shaft 122 such that a distal end of the catheter abuts the arms 129 of the locking pin 128 as shown in FIG. 16. The locking pin 128 is then pulled proximally such that the arms 129 collapse into the release catheter 134, transferring the locking pin 128 from its open position to its closed position and disengaging the arms from the openings in the locking shaft 122 as shown in FIG. 17. Once the release catheter 134 has enveloped the arms 129 of the locking pin 128, the inherent elasticity of the heart vessel may be used to pull release catheter and the locking pin apart, thus spacing the two anchors 116, 118 to a desired distance. The determination of a proper distance between the two anchors may be detected by ultrasound, either from outside the body, from the esophagus, or from inside the heart. An appropriate distance is one at which mitral regurgitation disappears or is as small as possible. Once an appropriate distance has been achieved, the release catheter 134 may be removed and the arms 129 may once again engage the openings 133 of the locking shaft 122 in its open position. The procedure for adjusting the length of the elongate body 110 may be repeated as many times as necessary to achieve a desired length. Additionally, the modification in length does not have to occur during a single procedure. The length of the elongate body 110 may be adjusted even after a period of hours, weeks, or months have passed.

In an alternate embodiment to the locking pin 128 described above, as shown in FIG. 18, a locking mechanism 135 includes a substantially diamond-shaped base 136 made of two resilient Nitinol strands, a head 137, a tail 139, and two locking spheres 138. The cinching thread 120 is attached to the tail 139 of the locking mechanism 135. In one embodiment, the cinching thread 120 is cut from the same tube of Nitinol as the distal anchor 118 and is formed as one piece therewith. The cinching thread 120 may also be welded, screwed or hooked to the tail 139. The head 137 of the locking mechanism 128 is a loop into which a pull line 124 is inserted. The two locking spheres 138 are attached at about the middle of the base 136 at the apex of the diamond shape and are adapted to fit into openings 133 of the locking shaft 122. The locking mechanism 135 has an open position and a closed position similar to the open and closed positions of the locking mechanism described above. Specifically, in the open position, the greatest distance between the locking spheres 138 is greater or about equal to the inner diameter of the locking shaft 122. In the closed position, the greatest distance between the locking spheres 138 is less than the inner diameter of the locking shaft 122. When a force is applied in the proximal direction by, for instance, pulling on the pull wire 124, the locking mechanism 135 will act as a ratchet and engage each successive opening 133.

With reference now to FIG. 19, in order to move the locking mechanism 135 in a distal direction, a release catheter 134 may be inserted into the locking shaft 122 so that a distal end of the catheter abuts the locking spheres 138. The catheter can be used to force the resilient base 136 of the locking mechanism 135 from its open position to its closed position, disengaging the locking spheres 138 from the openings 133 in the locking shaft 122 and allow the locking mechanism 135 to be moved distally. Subsequently, the release catheter 134 may be removed and the locking spheres 138 may once again engage the openings 133 of the locking shaft 122 in the open position.

With reference now to FIGS. 20 and 21, another alternate embodiment of a locking mechanism includes a beaded cinching suture 140 which extends between a proximal and a distal anchor (not shown) as described above. Additionally, a locking structure 144 may be attached to the proximal anchor. The locking structure 144 includes a housing 148 and jaws 146 which have a closed position and an open position. In the closed position, the jaws 146 are angled toward the center of the housing such that the distance between proximal ends 147 of the jaws is less than the diameter of a bead 142 on the beaded cinching suture 140. Additionally, in the closed position, distal ends 151 of the jaws 146 protrude past a surface of the housing 148 as shown in FIG. 21. In the open position, the distance between the proximal ends 147 of the jaws 146 is about equal to or greater than the diameter of a bead 142 on the beaded cinching suture 140. The jaws 146 are biased to be in the closed position. The housing 148 is adapted to receive the beaded cinching suture 140 which may be pulled proximally through the housing causing the distal stent to move proximally. As the beaded cinching suture 140 is pulled proximally through the housing 148, the jaws 146 are forced from their closed position to their open position, allowing the bead 142 to pass through them. After the bead 142 has passed through the jaws 146, the jaws resume their closed position.

As described above with respect to FIG. 15, a guide catheter may be used to provide a counter force as the beaded cinching suture 140 is pulled proximally through the housing. Further, this embodiment is not limited to the specific locking structure as described above, but rather the locking structure may be any housing adapted to receive the beaded cinching suture 140. For example, the housing may be made from a flexible material such as a biocompatible polymer which would allow the housing to expand to accept beads from the beaded cinching suture 140 as the suture is pulled the housing.

If it is necessary to move the beaded cinching suture 140 distally, a release catheter 153 with a diameter that is greater than the diameter of the housing 148 may be inserted into the coronary sinus. The release catheter 153 has a diameter such that it contacts the distal ends 151 of the jaws 146 and forces the jaws from the closed position to the open position. Once the jaws 146 are in the open position, the beaded cinching structure 140 may be moved distally. Once the housing 148 has been moved to a desired position along the beaded cinching suture 140, the release catheter 153 may be removed and the jaws 146 will return to their closed position.

Figure 22:
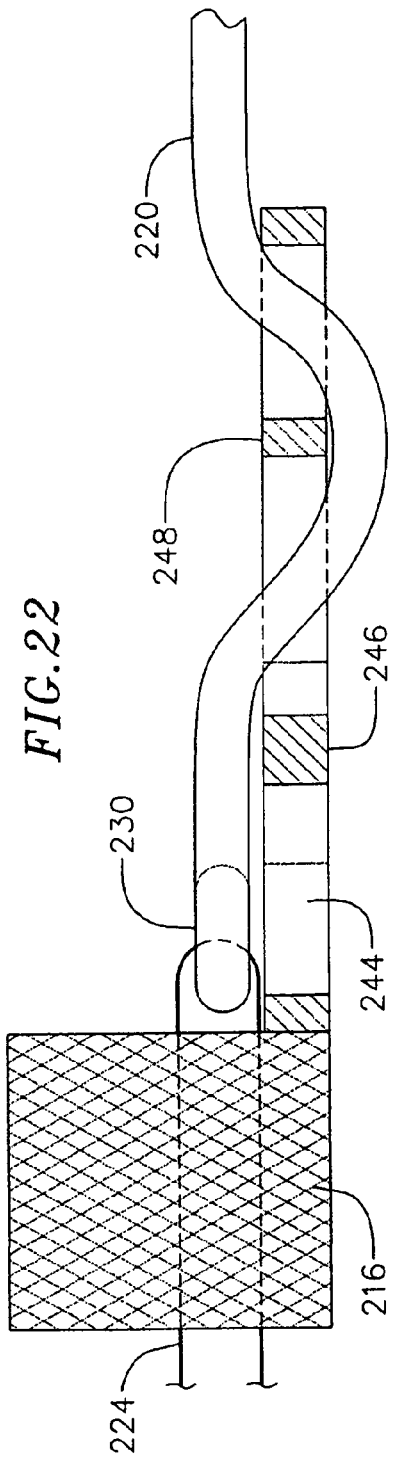
FIG. 22 is a schematic side view of an alternate embodiment of a locking mechanism of the present invention.
Figure 23:
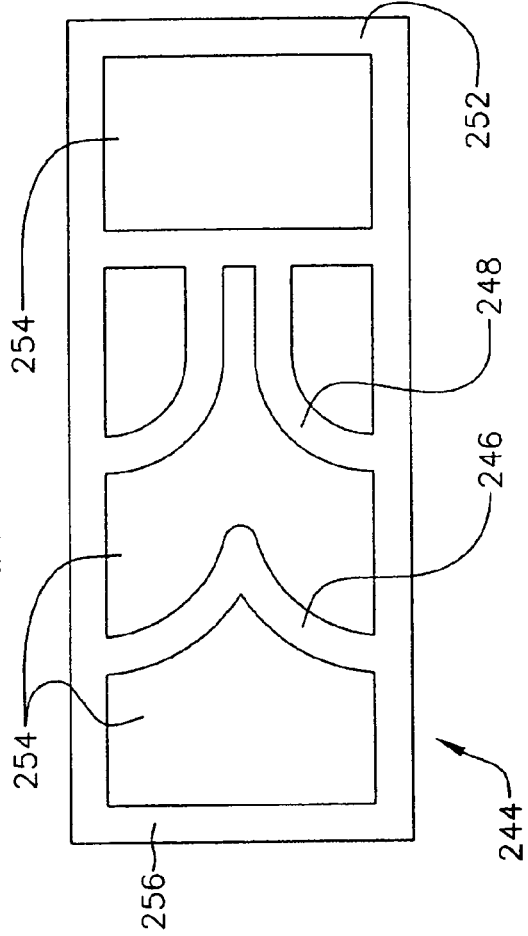
FIG. 23 is a detail of a top view of the locking mechanism of FIG. 22.
Figure 24:
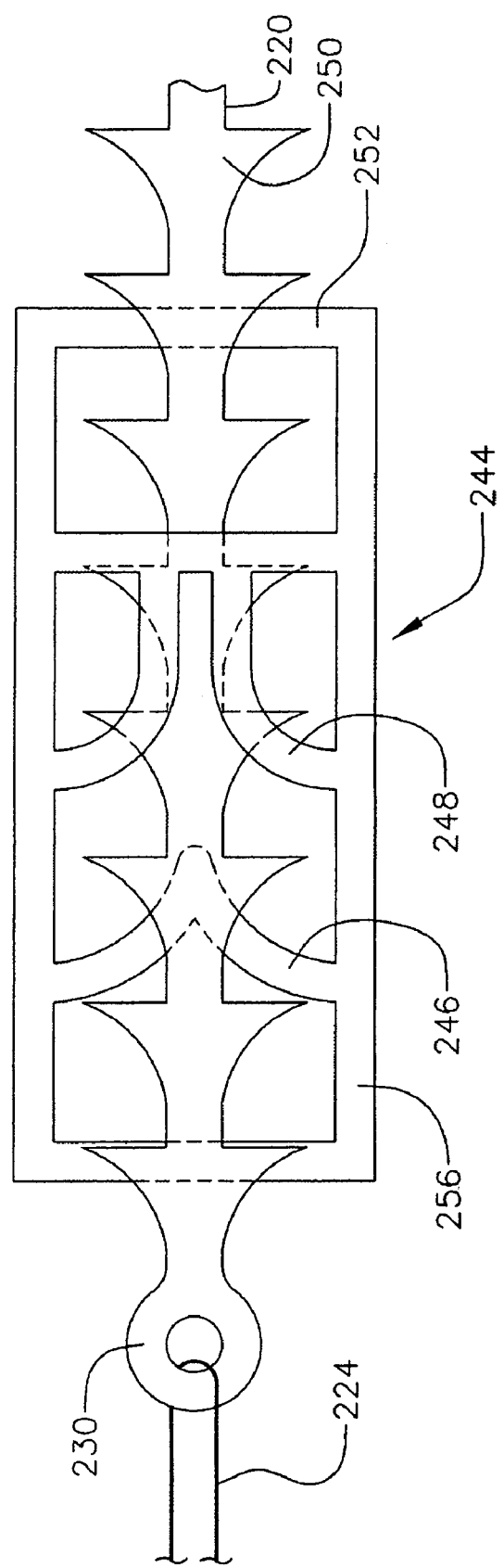
FIG. 24 is a detail of a top view of the locking mechanism of FIG. 22 including a cinching thread.

With reference now to FIGS. 22 through 24, another alternate embodiment of a locking mechanism includes a cinching thread 220 which extends between a proximal anchor 216 and a distal anchor (not shown) as described above. The structure of the cinching thread 220 includes a series of attached conical elements 250 (FIG. 24) and a head 230 to which a pull line 224 may be attached. Additionally as shown schematically in FIG. 22, a locking structure 244 is attached to the proximal anchor 216. As shown in more detail in FIGS. 23 and 24, the locking structure 244 includes a housing frame 256 having a proximal transverse beam structure 246 and a distal transverse beam structure 248 with openings 254 created between the housing frame 256 and the transverse beam structures 246, 248. The cinching thread 220 is woven through the locking structure 224 such that the thread is passed over the proximal transverse beam structure 246, under the distal transverse beam structure 248, and then over a distal end 252 of the locking structure 244. The proximal and distal transverse beam structures 246, 248 have a one-way valve shape such that the cinching thread 220 may be pulled proximally through the locking structure 244 to shorten the distance between the proximal and distal anchors, but the cinching thread will be prevented from being pulled distally.

While the foregoing describe exemplary embodiments of the invention, it will be obvious to one skilled in the art that various alternatives, modifications and equivalents may be practiced within the scope of the appended claims.

What is claimed is:

1. A device for the treatment of mitral annulus dilatation comprising:
   an elongate body having dimensions as to be insertable into a coronary sinus, the elongate body including:
   a proximal frame having a proximal anchor, the proximal anchor being transferable between a first state and a second state;
   a distal frame having a distal anchor, the distal anchor being transferable between a first state and a second state;
   a ratcheting strip attached to the distal frame, the ratcheting strip having alternating engagement portions and openings, the ratcheting strip having a semi-cylindrical cross section;
   an accepting member attached to the proximal frame, the accepting member insertable into the openings of the ratcheting strip and adapted to engage the engagement portions of the ratcheting strip; and
   an actuating member being adapted to engage the ratcheting strip and to move the ratcheting strip relative to the proximal anchor;
   wherein the diameters of the proximal anchor and the distal anchor are greater in the second state than in the first state;
   wherein the proximal anchor is adapted to allow the ratcheting strip to be pulled through it; and
   wherein the distal frame further comprises a bridge of X-shaped elements, wherein the bridge is more flexible than the ratcheting strip.

2. The device of claim 1 wherein the proximal anchor and the distal anchor are stents.

3. The device of claim 1 wherein the proximal anchor and the distal anchor are-baskets.

4. The device of claim 1 wherein the accepting member further includes a latch.

5. The device of claim 4 further comprising a release mechanism, the release mechanism including a release wire attached through a hole in the latch.

6. The device of claim 1 further comprising a guide catheter covering the elongate body.

7. The device of claim 1 wherein the diameters of the proximal anchor and the distal anchor in the second state are about equal to the diameter of the coronary sinus.

8. A device for the treatment of mitral annulus dilatation comprising:
   an elongate body having dimensions as to be insertable into a coronary sinus, the elongate body including:
   a proximal anchor, the proximal anchor being transferable between a first state and a second state;
   a distal anchor, the distal anchor being transferable between a first state and a second state;
   a tubular locking shaft attached to the proximal anchor, the tubular locking shaft having a plurality of alternating engagement portions and openings along a peripheral wall of the tubuar locking shaft;
   a cinching thread attached to the distal anchor;
   a locking pin attached to the cinching thread and being moveable through the tubular locking shaft, the locking pin having a plurality of locking segments insertable into the openings of the tubular locking shaft and adapted to engage the engagement portions of the tubular locking shaft; and
   a pull line attached to the locking pin, the pull line adapted to move the locking pin through the tubular locking shaft;
   wherein the diameters of the proximal anchor and the distal anchor are greater in the second state Than in the first state.

9. The device of claim 8 wherein the proximal anchor and the distal anchor are stents.

10. The device of claim 8 wherein the proximal anchor and the distal anchor are baskets.

11. The device of claim 8 wherein the diameters of the proximal anchor and the distal anchor in the second state are about equal to the diameter of the coronary sinus.

12. The device of claim 8 wherein the proximal anchor is adapted to allow the cinching thread to be pulled through it.

13. The device of claim 8 wherein the locking segments arms.

14. The device of claim 8 wherein the locking segments are spheres.

* * * * *